(12) United States Patent
Omata et al.

(10) Patent No.: US 8,313,840 B2
(45) Date of Patent: *Nov. 20, 2012

(54) MEDICAL DEVICE HAVING SURFACE LUBRICITY IN WET STATE

(75) Inventors: Kazuya Omata, Fujinomiya (JP); Naoyuki Maeda, Fujinomiya (JP); Makoto Onishi, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/186,117

(22) Filed: Jul. 19, 2011

(65) Prior Publication Data
US 2011/0274918 A1 Nov. 10, 2011

Related U.S. Application Data

(63) Continuation of application No. PCT/JP2010/051056, filed on Jan. 27, 2010.

(30) Foreign Application Priority Data

Jan. 28, 2009 (JP) ................. 2009-017060

(51) Int. Cl.
*B32B 9/04* (2006.01)
*B32B 15/04* (2006.01)

(52) U.S. Cl. ...................... 428/457; 428/461
(58) Field of Classification Search .............. 428/336, 428/457, 461, 463; 514/772.3, 579, 740
See application file for complete search history.

(56) References Cited

U.S. PATENT DOCUMENTS
5,670,558 A   9/1997  Onishi et al.
6,828,028 B1 * 12/2004  Fukui et al. ................. 428/413

FOREIGN PATENT DOCUMENTS
JP  8-019599 A  1/1996
JP  8-033704 A  2/1996
JP  2000-039737 A  2/2000
JP  2007-267757 A  10/2007
WO  WO 2009058079 A1 * 5/2009

OTHER PUBLICATIONS

International Search Report (PCT/ISA/210) issued on Mar. 16, 2010, by Japanese Patent Office as the International Searching Authority for International Application No. PCT/JP2010/051056.

* cited by examiner

*Primary Examiner* — Thao T. Tran
(74) *Attorney, Agent, or Firm* — Buchanan Ingersoll & Rooney PC

(57) ABSTRACT

A medical device wherein a metal base and a surface lubricating layer are fixed with each other more firmly. The medical device permanently exhibits excellent surface lubricity when in use. A medical device which has a lubricating surface when wet, is characterized by comprising a base layer which is composed of a metal material, an intermediate layer which covers at least a part of the base layer and is composed of a compound that has a plurality of thiol groups in each molecule, and a surface lubricating layer which covers the surface of the intermediate layer and is composed of a hydrophilic polymer that has a reactive functional group. The medical device is also characterized in that the surface lubricating layer is bonded to the base layer via the intermediate layer by reacting the compound having thiol groups with the hydrophilic polymer.

7 Claims, 15 Drawing Sheets

MEDICAL DEVICE HAVING SURFACE LUBRICITY IN WET STATE

This application is a continuation of International Application No. PCT/JP2010/051056 filed on Jan. 27, 2010, and claims priority to Japanese Application No. 2009-017060 filed on Jan. 28, 2009, the entire content of both of which is incorporated herein by reference.

TECHNICAL FIELD

This invention generally relates to a medical device. More particularly, the invention involves a medical device whose surface exhibits lubricity in a wet state.

BACKGROUND DISCUSSION

Medical devices to be inserted into a living body, such as catheters, guide wires and the like, can exhibit excellent lubricity in order that damage of tissues such as blood vessels is reduced and handleability by an operator is improved. Hence, there have been developed and put into practice methods of coating a base material surface with a hydrophilic polymer having lubricity. In such medical devices, elution and peeling-off of the hydrophilic polymer from the base material surface present a problem in maintaining safety and handleability.

In order to avoid such a problem, Japanese Patent Laid-Open No. Hei 8-33704 discloses a medical device wherein a water-soluble or water-swelling polymer is dissolved in a solvent capable of swelling a base material of the medical device to prepare a polymer solution, and the base material of the medical device is swollen by immersion in the polymer solution, followed by crosslinking or converting the polymer into a higher molecular weight product on the base material surface, thereby forming a surface lubricating layer on the base material surface.

In the method described in the above-indicated Japanese Patent Laid-Open No. Hei 8-33704, the surface lubricating layer can be strongly fixed on the base material to some extent. Especially where the base material is made of a polymer material and the base material per se is swollen with a hydrophilic polymer solution, very strong fixing is enabled by the formation of an interpenetrating network structure of the base material polymer and the hydrophilic polymer formed as the surface lubricating layer. On the other hand, where the base material is made of a metal material, the hydrophilic polymer serving as the surface lubricating layer is fixed on the base material only by the insolubilizing effect, involving a higher risk that the surface lubricating layer is peeled off when compared with the polymer base material. Thus, there is a need for a coating method wherein a hydrophilic polymer can be fixed more strongly on a metal base surface.

A known method of fixing a hydrophilic polymer on a metal base involves carrying out a primer treatment. For instance, Japanese Patent Laid-Open No. 2007-267757 discloses a method wherein a base metal is pre-treated with a primer including, as an essential component, an adhesive organic compound having, in the molecule, at least one functional group capable of adsorption on a metal and at least one reactive functional group and a film of a hydrophilic polymer is formed thereon to improve adhesion between the surface lubricating layer and the metal base.

However, the method set out in the above-mentioned Japanese Patent Laid-Open No. 2007-267757 has had a problem in that the surface lubricating layer is not sufficiently strongly fixed on the metal base.

SUMMARY

A medical device disclosed herein can relatively permanently show excellent surface lubricity in use by more strongly fixing a metal base and a surface lubricating layer together.

One disclosed example of a medical device having surface lubricity in wet state includes a base layer made of a metal material, an intermediate layer that covers at least a part of the base layer and is made of a compound having a plurality of thiol groups (—SH: which may be sometimes called a mercapto group, a sulfhydryl group or a hydrosulfide group) in the molecule, and a surface lubricating layer that covers a surface of the intermediate layer and is made of a hydrophilic polymer having a reactive functional group, wherein the surface lubricating layer is bonded (fixed) to the base layer via the intermediate layer by reaction between the compound having the thiol groups and the hydrophilic polymer.

The compound having a plurality of thiol groups in the molecule has 3 or more thiol groups in one molecule.

According to one possibility, the hydrophilic polymer has a reactive domain wherein the reactive functional groups gather together and a hydrophilic domain wherein hydrophilic monomers gather together.

According to a disclosed example, a medical device exhibiting surface lubricity in wet state includes a base layer made of a metal material, and a surface lubricating layer that covers at least a part of the base layer, wherein the surface lubricating layer is obtained by forming a crosslinked structure by reaction between a compound having a plurality of thiol groups in the molecule and a hydrophilic polymer having a reactive functional group and the surface lubricating layer is bonded to the metal base via the thiol group left in the crosslinked structure.

The surface lubricating layer can be obtained by coating, onto the base layer, a mixed solution dissolving the compound having a plurality of thiol groups in the molecule and the hydrophilic polymer having a reactive functional group in a solvent and subsequently reacting the thiol groups and the reactive functional group.

BRIEF DESCRIPTION OF THE DRAWING FIGURES

DETAILED DESCRIPTION

One example of a medical device having surface lubricity in a wet state as disclosed here includes a base layer made of a metal material, an intermediate layer that covers at least a part of the base layer and is made of a compound having a plurality of thiol groups in the molecule, and a surface lubricating layer that covers at least a part of the intermediate layer and contains a hydrophilic polymer having a reactive functional group, wherein the surface lubricating layer is bonded (fixed) to the base layer via the intermediate layer by reaction between the compound having the thiol groups used as a constituent component of the intermediate layer and the hydrophilic polymer having the reactive functional group.

Such a configuration can be provided, for example, wherein after the formation of the intermediate layer by bonding the compound having a plurality of thiol groups in the molecule to the surface of the metal base, the reactive functional group of the hydrophilic polymer (e.g. an epoxy group) and the residual thiol group of the intermediate layer are reacted thereby forming the surface lubricating layer. In doing so, the surface lubricating layer can be strongly fixed to the metal base through the intermediate layer, thus enabling excellent surface lubricity to be permanently shown when in use.

Figure 1A:
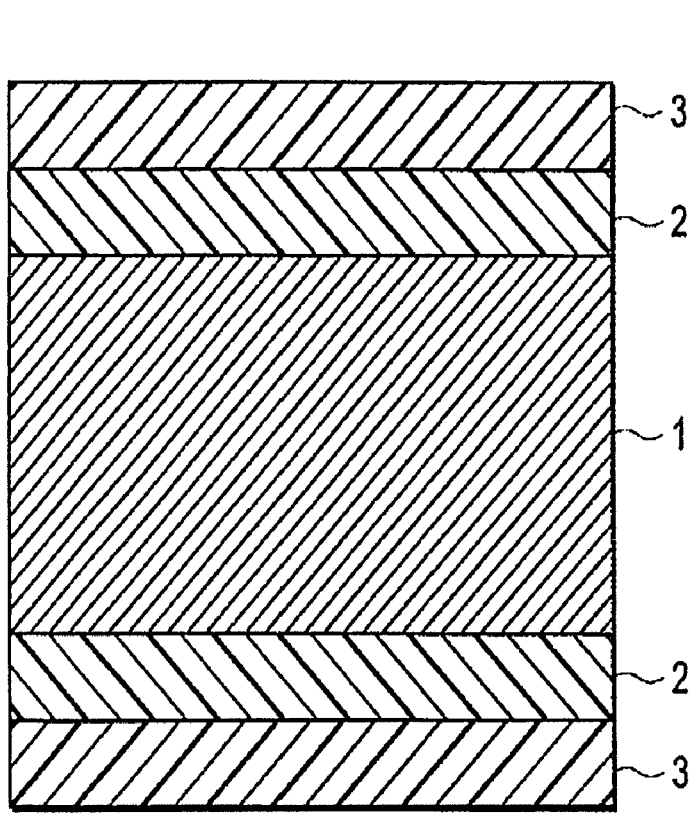
FIG. 1A is a partial sectional view schematically showing a laminate structure of a surface according to one embodiment of a medical device exhibiting surface lubricity in a wet state which is disclosed by way of example.
Figure 1B:
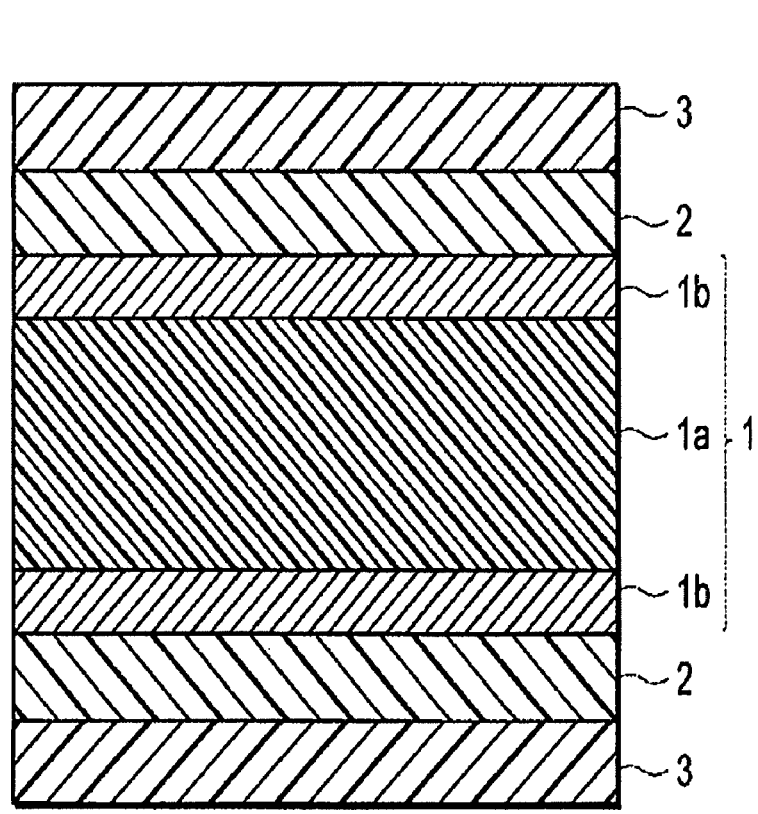
FIG. 1B is a partial sectional view schematically showing another laminate structure of a surface according to the one embodiment disclosed by way of example.

FIG. 1A is a partial sectional view schematically showing one example of a laminate structure of a surface of a medical device having surface lubricity in a wet state (which may be referred to herein simply as medical device). FIG. 1B is a partial sectional view schematically showing another example of a laminate structure of a surface of a medical device.

As shown in FIGS. 1A and 1B, this disclosed example of the medical device 10 includes a base layer 1 made of a metal material, an intermediate layer 2 covering at least a part of the base layer 1 (in the figures, an instance of wholly covering the base layer within the figures is shown) and made of a compound having a plurality of thiol groups in the molecule, and a surface lubricating layer 3 covering the surface of the intermediate layer 2 and made of a hydrophilic polymer having a reactive functional group. The surface lubricating layer 3 is bonded to the base layer 1 through the intermediate layer 2 by reaction between the compound having the thiol groups and the hydrophilic polymer.

Each constituent member of the medical device of this disclosed example is hereinbelow described in detail.

(1) Base Layer 1

The base layer 1 of the medical device can be made of a metal material.

(1a) Configuration of the Base Layer 1

The base layer 1 "made of a metal material" means that at least a surface of the base layer 1 can be constituted of a metal material, and is not limited in any way to one wherein the base layer 1 is entirely (fully) constituted (formed) of a metal material. Accordingly, as shown in FIG. 1B, the surface metal layer 1b, which is framed by coating the surface of a base layer core portion 1a, formed of a resin material, with a metal material by an appropriate method (for example, plating, metal deposition, sputtering or the like), is also embraced within the scope of the base layer 1. Accordingly, the base layer core portion 1a can be in the form of a multi-layered structure wherein multiple layers of different types of materials are laminated, or a structure (composite body) wherein members formed of different types of materials for individual portions of a medical device are connected with one another. Moreover, a different type of middle layer (not shown) may be further formed between the base layer core portion 1a and the surface metal layer 1b. Additionally, as to the surface metal layer 1b, it may be in the form of a multi-layered structure wherein multiple layers of different types of metal materials are laminated, or a structure (composite body) wherein members formed of different types of metal materials for individual portions of a medical device are connected with one another.

(1b) Configuration of the Base Layer Core Portion 1a

No specific limitation is placed on the type of material usable for the base layer core portion 1a, and a material capable of satisfactorily developing a function as an optimal base layer core portion 1a can be appropriately chosen depending on, for example, the application as a catheter, a guide wire, an injection needle or the like. For example, there can be exemplified various types of organic (polymer) materials including polyolefins, modified polyolefins, polyethers, polyurethanes, polyamides, polyimides, polyesters and copolymers thereof, inorganic (polymer) materials such as various types of ceramic materials, and organic-inorganic composite materials although not limited thereto.

(1c) Configurations of the Base Layer 1 or the Surface Metal Layer 1b

The metal materials usable as the base layer 1 or the metal coating layer 1b are not specifically limited and can include metals capable of bonding to the thiol group such as, for example, various types of stainless steels (SUS) such as SUS304, gold, platinum, silver, copper, nickel, cobalt, titanium and alloys thereof such as nickel-titanium (Ni—Ti) alloy, nickel-cobalt (NI—Co) alloy and the like. These may be used singly or in combination of 2 or more. A suitable metal material for an intended end use as a metal base of a catheter, a guide wire, an injection needle or the like can be appropriately chosen.

The base layer is not specifically limited in shape and can be selected from, for example, sheet, wire, tubular forms and the like depending on the manner of use.

(1d) Configuration of the Middle Layer

The material usable as the middle layer (not shown) is not specifically limited. It is possible to select from materials capable of satisfactorily developing the function of bonding between the base layer core portion 1a and the surface metal layer 1b is possible. For example, there may be exemplified organic (polymer) materials such as polyolefins, modified polyolefins, polyethers, polyurethanes, polyamides, polyimides, polyesters and copolymers thereof, inorganic (polymer) materials such as various types of ceramic materials, and organic-inorganic composite body although not limited thereto in any way.

(2) Intermediate Layer 2

The intermediate layer 2 for the medical device of this embodiment can be made of a compound covering at least a part of the base layer 1 and having a plurality of thiol groups in the molecule.

The reason why the intermediate layer 2 covers at least a part of the base layer 1 is as follows: in the medical device for the intended end usage as a catheter, a guide wire, an injection needle or the like, it is not always required that all the surfaces (entire surface) of these medical devices have lubricity in wet state, but it suffices that the intermediate layer 2 is formed to cover only a surface portion (either a part or all), which is required to have surface lubricity in wet state.

(2a) Thickness of the Intermediate Layer 2

The thickness of the intermediate layer 2 constituting the medical device of the embodiment can be sufficient to enable the base layer 1 made of a metal material and the surface lubricating layer 3 to be strongly fixed through the intermediate layer 2 and to permanently show excellent surface lubricity in use. For example, the thickness is below 10 μm, for example, below 10 μm. If effectively functioned as a so-called molecular adhesive, the thiol compound can be in the state of being formed as a monomolecular film layer on the surface of the base layer 1 (=One molecule of the thiol compound along a direction of the thickness).

(2b) Constituent Member of the Intermediate Layer 2 (Thiol Compound)

As a "compound having a plurality of thiol groups in the molecule" (also referred to herein as "thiol compound") forming the intermediate layer 2, no limitation is placed thereon, and the thiol compound has a plurality of thiol groups in the molecule. For example, the compound has such a structure that when the thiol group is bonded to the surface of the base layer 1, the residual thiol group is likely to be exposed at the outermost surface of the intermediate layer 2 so as to permit easy reaction between the residual thiol group and the reactive functional group of a hydrophilic polymer of the surface lubricating layer 3. From such a standpoint, the thiol compound may be one having 2 or more thiol groups in the molecule (see, by comparison, FIGS. 4, 6 and 7 which are the results of the evaluation tests of the surface lubrication retention of Examples 1 to 3 having 2 or more thiol groups and FIG. 8 which is the result of the evaluation test of the surface lubrication retention of Comparative Example 2 having one thiol group), for example, 2 to 20 thiol groups in one molecule, for example, 3 to 10 thiol groups, for example, 3 to 6 thiol groups (see, by comparison, FIGS. 4 and 6 which are the results of the evaluation tests of the surface lubrication retention of Examples 1 and 2, respectively, having 3 and 6 thiol groups and FIG. 7 which is the result of the evaluation test of the surface lubrication retention of Example 3 having 2 thiol groups).

From this viewpoint, the thiol compounds are not specifically limited and may be, for example, any of linear, branched linear and cyclic compounds. Examples include compounds having 2 thiol groups in the molecule such as 1,2-ethanedithiol, 1,2-propanedithiol, 1,3-propanedithiol, 1,4-butanedithiol, 2,3-butanedithiol, 1,5-pentanedithiol, 1,6-hexanedithiol, 1,8-octanedithiol, 3,6-dioxa-1,8-octanedithiol, bis(2-mercaptoethyl)ether, bis(2-mercaptoethyl)sulfide, 1,2-benzenedithiol, 1,4-benzenedithiol, 1,4-bis(mercaptomethyl)benzene, toluene-3,4-dithiol, 1,5-dimercaptonaphthalene, 2,6-dimercaptopurine, 4,4'-biphenyldithiol, 4,4'-thiobisbenzenethiol, tetraethylene glycol bis(3-mercaptopropionate) and the like, compounds having 3 thiol groups in the molecule such as 1,3,5-benzenetrithiol, tris-[(3-mercaptopropionyloxy-ethyl)-isocyanurate, triazine trithiol, trimethylolpropane tris(3-mercaptopropionate) (TMMP) and the like, compounds having 4 thiol groups in the molecule such as pentaerythritol tetrakis(mercaptoacetate), pentaerythritol tetrakis(3-mercaptopropionate) and the like, compounds having 6 thiol groups in the molecule such as dipentaerythritol hexakis(3-mercaptopropionate) and the like, and derivatives and polymers thereof. These may be used singly or in combination of 2 or more. For example, mention is made of tris-[(3-mercaptopropionyloxy)-ethyl]-isocyanurate and dipentaerythritol hexakis(3-mercaptopropionate). These are compounds, which have such a structure that residual thiol groups are likely to be exposed at the outermost surface so that the residual thiol groups and the reactive functional group of a hydrophilic polymer are likely to be reacted with each other when the thiol groups are bonded to the surface of the base layer, and which also have a stable molecular skeleton and good affinity for the surface of the base layer and have 3 to 6 thiol groups.

In this embodiment disclosed by way of example, the thiol compounds are not limited to the above-exemplified ones in any way, and other types of thiol compounds may also be usable, for example, if they can effectively develop the effect of the invention.

(2c) Method for Forming the Intermediate Layer 2

For the formation of the intermediate layer 2, the base layer 1 made of a metal material is immersed in a solution dissolving a thiol compound therein (which may be hereinafter referred to simply as "thiol compound solution") and dried to form the intermediate layer 2 made of the thiol compound on the surface of the base layer 1 made of the metal material. It will be noted that if the system is reduced in pressure for defoaming in a state of the base layer 1 being immersed in the thiol compound solution, the solution can be quickly infiltrated into the fine, narrow inner surfaces of a medical device such as a catheter, a guide wire, an injection needle or the like thereby permitting the coating of the intermediate layer 2 to be facilitated.

Oils and fats and dirt, attached to the surface of the base layer 1, can be removed prior to the immersion of the base layer 1 in the thiol compound solution. For example, it can be desirable to clean the surface of the base layer 1 by an appropriate method. For such surface cleaning of the base layer 1, there can be exemplified a method of ultrasonic cleaning in a solvent such as acetone although not limited thereto.

In an exemplary embodiment, in case where the intermediate layer 2 is formed only on a part of the base layer 1 made of a metal material, only the part of the base layer 1 made of a metal material can be immersed in a thiol compound solution and dried to form the intermediate layer 2 made of a thiol compound only at a desired surface portion of the base layer 1 made of a metal material.

If, for example, immersing only a part of the base layer 1 made of the metal material in a thiol compound solution is difficult, the intermediate layer 2 made of a thiol compound can be formed on a desired surface portion of the base layer 1 by preliminarily protecting (covering) a surface portion of the base layer 1, which is not to be formed with the intermediate layer 2, with an attachable and detachable appropriate member or material, followed by immersing the base layer 1 in a thiol compound solution, drying and removing the protecting member (material) from the surface portion of the base layer 1 not to be formed with the intermediate layer 2. In this regard, however, the invention should not be construed as limited thereto, but the intermediate layer 2 can be formed by appropriately using hitherto known methods.

(2c-1) Concentration of the Thiol Compound Solution

In view of uniform coating in a desired thickness, for example, the concentration of a thiol compound in the thiol compound solution can be, for example, 0.001 to 20 wt %, for example, 0.01 to 10 wt %. If the concentration of the thiol compound is less than 0.001 wt %, a satisfactory amount of the thiol compound typically cannot be bonded to the surface of the base layer 1, with some difficulty in that the surface lubricating layer 3 is strongly fixed on the base layer 1. Where the concentration of the thiol compound exceeds 20 wt %, the viscosity of the thiol compound solution becomes too high, with concern that a uniform film cannot be coated and thus, a difficulty may be involved in quickly coating a fine, narrow inner surface of a medical device such as a catheter, a guide wire, an injection needle or the like. In this regard, however, a concentration outside the above range may be adequately used if it is within a range not influencing the effect of the invention.

(2c-2) Solvent Used in the Thiol Compound Solution

As a solvent used for the thiol compound solution, no limitation is placed. Mention is made, for example, of water, alcohols such as methanol, ethanol, isopropanol, ethylene glycol and the like, ketones such as acetone, methyl ethyl ketone and the like, esters such as ethyl acetate and the like, halides such as chloroform and the like, olefins such as butane, hexane and the like, ethers such as tetrahydrofuran, butyl ether and the like, aromatic compounds such as benzene, toluene and the like, and amides such as N,N-dimethylformamide (DMF) and the like although not limited thereto. These may be used singly or in combination of 2 or more.

(2c-3) Drying Conditions Used for the Formation of the Intermediate Layer 2

Drying conditions for the formation of the intermediate layer 2 can be employed. For example, if the thiol compound solution is likely to be evaporated, natural drying can be satisfactorily used or forced drying treatment such as under heating or reduced pressure may be carried out. It will be noted that where a thiol compound has polymerizability, it is possible to polymerize the thiol compound simultaneously with drying when heated. Where a thiol compound is polymerized, an additive such as a thermal polymerization initiator or the like may be preliminarily added to the thiol compound solution in appropriate amounts.

During or after drying, the thiol compound may be polymerized by a method other than heating. The method other than heating includes, for example, UV irradiation, electron beam irradiation, plasma irradiation or the like.

After the formation of the intermediate layer 2, excess thiol compound may be washed away by means of an appropriate solvent so as to leave the thiol compound alone bonded to the surface of the base layer 1 made of metal material.

(3) Surface Lubricating Layer 3

The surface lubricating layer 3 constituting the medical device of this embodiment is made of a hydrophilic polymer covering the surface of the intermediate layer 2 and having a reactive functional group. The hydrophilic polymer can have a reactive domain where the reactive functional groups gather together and a hydrophilic domain where hydrophilic monomers gather together.

The hydrophilic polymer serving as the surface lubricating layer 3 and having a reactive functional group (which is hereinafter referred to simply as "hydrophilic polymer") can be formed to cover the surface (entirety) of the intermediate layer 2. In this regard, however, where the intermediate layer 2 is formed over the entire surface of the base layer 1 including a surface portion which is required to have surface lubricity in wet state, the surface lubricating layer 3 may be formed only at a surface portion (which may be a part or a whole) of the surface of the intermediate layer 2 required to have surface lubricity in wet state.

(3a) Thickness of the Surface Lubricating Layer 3

The surface lubricating layer 3 constituting the medical device of the embodiment can have a thickness, for example, only enough to permanently show excellent surface lubricity in use. The thickness of the surface lubricating layer 3 in non-swollen state can be 0.5 to 5 µm, for example, 1 to 5 µm, for example, 1 to 3 µm. If the thickness of the surface lubricating layer 3 in non-swollen state is less than 0.5 µm, it can be difficult to form a uniform film, with some case where surface lubricity in wet state is not satisfactorily shown. On the other hand, when the thickness of the surface lubricating layer 3 in non-swollen state exceeds 5 µm, there is concern that when medical device is inserted into the blood vessel or the like within a living body, swelling of such a thick surface lubricating layer may lead to the damage of the inner tissue of the blood vessel or the like, or is unlikely to permit passage of the medical device upon passage through a site (for example, an interior of peripheral vessel or the like) wherein a clearance between the blood vessel or the like and the medical device is small.

(3b) Hydrophilic Polymer

The hydrophilic polymer forming the surface lubricating layer 3 and having a reactive functional group may be obtained, for example, by copolymerization of a monomer having a reactive functional group in the molecule and a hydrophilic monomer.

The hydrophilic polymer according to an exemplary embodiment may be either a homopolymer composed of repeating units of 1 type or a copolymer composed of repeating units of 2 or more types, which may be a star-like, comb-like, random, graft, cyclic, block copolymer and the like. For example, mention is made of copolymers composed of 2 or more types of repeating units, for example, binary copolymers, for example, graft copolymers and block copolymers.

For example, forms of the hydrophilic polymer include block or graft copolymers from the standpoint that monomers having a reactive functional group (repeating units having a reactive functional group) gather together to form a reactive domain and hydrophilic monomers (repeating units having a hydrophilic site in a hydrophilic polymer) gather together to form a hydrophilic domain. With the block or graft copolymer, good results are obtained in respect of the strength and lubricity of the surface lubricating layer.

As to the method of preparing (polymerization method) these hydrophilic polymers, no limitation is placed thereon. The preparation is feasible by application of conventionally known polymerization methods such as, for example, a living radical polymerization method, a polymerization method using macromonomers, a polymerization method using a polymerization initiator such as a macro azo initiator or the like, a polycondensation method and the like.

(3b-1) Monomer Having a Reactive Functional Group

As such a monomer having the above reactive functional group, no limitation is placed thereon so far as it has reactivity with a thiol group. For example, mention is made of monomers having an epoxy group such as glycidyl acrylate, glycidyl methacrylate and the like, and monomers having an isocyanate group in the molecule, such as acryloyloxyethyl isocyanate. Of these, monomers having an epoxy group, such as glycidyl acrylate, glycidyl methacrylate and the like, can be used in an exemplary embodiment. This is because they have, as a reactive functional group, an epoxy group that is excellent in reactivity with a thiol group, the reaction is promoted by application of heat, a crosslinked structure is formed and thus becomes insolubilized to easily form a surface lubricating layer, and handling is relatively easy. The hydrophilic polymer making use of monomers having an epoxy group is gentler in reaction rate (appropriate rate) in the course of the reaction such as by heating operations than hydrophilic polymers making use of monomers having an isocyanate group in the molecule. Accordingly, because the reaction rate is so gentle (appropriate rate) as to suppress or control the lowering of lubricity ascribed to the rise of a crosslinking density of the surface lubricating layer after gelation or solidification by immediate reaction in the course of the reaction such as under heating operations or in the course of the reaction with a thiol compound or mutual crosslinking reaction between reactive functional groups, handleability is considered as good. The monomers having these reactive functional group may be used singly or in combination of 2 or more.

(3b-2) Hydrophilic Monomer

As a hydrophilic monomer, any one may be used so far as it develops lubricity in a body fluid or an aqueous solvent and thus, no limitation is placed thereon. Mention can be made, for example, of acrylamide and derivatives thereof, vinyl pyrrolidone, acrylic acid or methacrylic acid and derivatives thereof, and monomers having a sugar or phospholipid at a side chain. For example, there can be exemplified N-methylacrylamide, N,N-dimethylacrylamide, acrylamide, acryloyl morpholine, N,N-dimethylaminoethyl acrylate, vinyl pyrrolidone, 2-methacryloyloxyethylphosphoryl choline, 2-methacryloyloxyethyl-D-glucoside, 2-methacryloyloxyethyl-D-mannoside, vinyl methyl ether, hydroxyethyl methacrylate and the like. From the standpoint of the ease in synthesis and operability, N,N-dimethylacrylamide can be employed. These hydrophilic monomers may be used singly or in combination of 2 or more.

(3c) Method for Forming the Surface Lubricating Layer 3 (Bonding Forms of Between the Base Layer 1-the Surface Lubricating Layer 3)

An embodiment disclosed by way of example can include the afore-stated base layer 1, intermediate layer 2 and surface lubricating layer 3, wherein the thiol compound and the hydrophilic polymer are reacted to bond the surface lubricating layer 3 to the base layer 1 through the intermediate layer 2.

Accordingly, where the surface lubricating layer 3 is formed, the base layer 1, on which the intermediate layer 2 has been fixed, can be immersed in a solution dissolving a hydrophilic polymer (hereinafter referred to simply as "hydrophilic polymer solution"), and thermally treated. By this, the reactive functional group (for example, an epoxy group) of the hydrophilic polymer and the residual thiol group of the intermediate layer 2 are reacted, thereby enabling the surface lubricating layer 3 to be bonded to the base layer 1 through the intermediate layer 2 simultaneously with the formation of the surface lubricating layer 3. It will be noted that if the system is reduced in pressure for defoaming in a state of immersing the base layer 1, fixed with the intermediate layer 2, in a hydrophilic polymer solution, the formation of the surface lubricating layer 3 can be facilitated by quickly impregnating the solution in a fine, narrow inner surface of the medical device such as a catheter, a guide wire, an injection needle or the like.

It will also be noted that in the embodiment disclosed by way of example here, where the surface lubricating layer 3 is formed only at part of the intermediate layer 2, only the part of the intermediate layer 2, fixed on the base layer 1, is immersed in the hydrophilic polymer solution and subjected to heat treatment or the like, thereby enabling the surface lubricating layer 3 made of the hydrophilic polymer to be formed on a desired surface portion of the intermediate layer 2.

If it is difficult to immerse only a part of the intermediate layer 2, fixed on the base layer 1, in the hydrophilic polymer solution, the intermediate layer 2 fixed on the base layer 1 can be immersed in the hydrophilic polymer solution after preliminary protection (coverage) of the surface portion of the intermediate layer 2, on which the surface lubricating layer 3 should not be formed, with an attachable and detachable member or material. Thereafter, the protecting member (material) on the surface portion of the intermediate layer 2, which is not to be formed with the surface lubricating layer 3, is removed and subsequently subjected to heat treatment or the like, thereby forming the surface lubricating layer 3 made of a hydrophilic polymer on a desired surface portion of the intermediate layer 2. In this regard, however, the invention is not limited to these formation methods, but the surface lubricating layer 3 can be formed by appropriately using hitherto known methods.

(3c-1) Concentration of the Hydrophilic Polymer Solution

The concentration of the hydrophilic polymer solution used for the formation of the surface lubricating layer 3 is not specifically limited. From the standpoint of uniform coating in a desired thickness, for example, the concentration of a hydrophilic polymer in the hydrophilic polymer solution can be 0.1 to 20 wt %, for example, 0.5 to 15 wt %, for example, 1 to 10 wt %. If the concentration of the hydrophilic polymer solution is less than 0.1 wt %, there is concern that such immersion operations as set out above have to be repeated in plural times so as to obtain the surface lubricating layer 3 of a desired thickness thereby lowering the production efficiency. On the other hand, when the concentration of the hydrophilic polymer solution exceeds 20 wt %, there is also concern that the viscosity of the hydrophilic polymer solution becomes too high to coat a uniform film and that a difficulty is involved in quickly coating a fine, narrow inner surface of a medical device such as a catheter, a guide wire, an injection needle or the like. In this regard, however, a concentration outside the above range may be adequately usable so far as it is within a range not influencing the effect of the invention.

(3c-2) Solvent Used for the Hydrophilic Polymer Solution

The solvents used for dissolution of a hydrophilic polymer solution are not specifically limited and can include, for example, N,N-dimethylformamide (DMF), chloroform, acetone, tetrahydrofuran, dioxane, benzene and the like although not limited thereto. These may be used singly or in combination or 2 or more.

(3c-3) Reaction Conditions (Heating Conditions) for Forming the Surface Lubricating Layer 3

For the formation of the surface lubricating layer 3, the reactive functional group (for example, an epoxy group) of a hydrophilic polymer and the residual thiol group of the intermediate layer 2 can be reacted under heat treatment or the like. Such heat treatment conditions (reaction conditions) can be capable of causing (promoting) the reaction between the reactive functional group of the hydrophilic polymer and the residual thiol group of the intermediate layer 2. For example, the heat treatment is carried out at not lower than 40° C., for example, 50° C. to 150° C. and for 15 minutes to 15 hours, for example, 30 minutes to 10 hours. If the heating temperature is lower than 40° C., there is concern that the reaction between the reactive functional group of a hydrophilic polymer and the residual thiol group of the intermediate layer 2 becomes slow. If the heating time is less than 15 minutes, the reaction scarcely proceeds, with concern that an unreacted hydrophilic polymer increases in amount, with some possibility that it becomes difficult to keep the surface lubricity over a long time. On the other hand, when the heating time exceeds 15 hours, a further effect ascribed to the heating is not expected, thus being poor in economy.

No limitation is placed on the pressure conditions when in heat treatment. The treatment may be carried out not only under a normal pressure (atmospheric pressure), but also under increased pressure or under reduced pressure. Where the reactive functional group of a hydrophilic polymer is an epoxy group, a reaction catalyst such as a trialkylamine compound or a tertiary amine compound such as pyridine or the like may be added to a hydrophilic polymer solution timely in an appropriate amount so as to promote the reaction with the residual thiol group of the intermediate layer 2. For a heating means (apparatus), there can be utilized, for example, an oven, a dryer, a microwave heating apparatus and the like.

Aside from the heat treatment, other methods of promoting the reaction between the reactive functional group of a hydrophilic polymer and the residual thiol group of the intermediate layer 2 may be mentioned and can be employed including, for example, the use of light, an electron beam, a radiation and the like, although not limited thereto in any way.

After the formation of the surface lubricating layer 3, an excess hydrophilic polymer may be cleaned with an appropriate solvent thereby permitting the hydrophilic polymer alone, in the form of the surface lubricating layer 3 strongly fixed on the base layer 1 through the intermediate layer 2, to be left thereat.

The thus formed surface lubricating layer 3 can develop lubricity after absorption of water at a body temperature of a patient (for example, 30 to 40° C.).

An embodiment of a medical device having surface lubricity in a wet state as disclosed here includes a base layer made of a metal material, and a surface lubricating layer covering at least a part of the base layer, wherein the surface lubricating layer is obtained by forming a crosslinked structure by reaction between a compound having a plurality of thiol groups in the molecule and a hydrophilic polymer having a reactive functional group, and the surface lubricating layer is bonded to the base layer through the thiol group left in the crosslinked structure.

According to an embodiment disclosed here by way of example, such a configuration can be provided wherein the metal base is immersed in a mixed solution dissolving, in a solvent, a compound having a plurality of thiol groups and a hydrophilic polymer having a reactive functional group (for example, an epoxy group) and subjecting to reaction between the compound having the thiol group and the hydrophilic polymer such as by heating operations, so that the surface lubricating layer can be formed simultaneously with the thiol group being bonded to the surface of the metal base. In doing so, the surface lubricating layer can be strongly fixed to the metal base thereby permanently showing surface lubricity in use.

Such embodiment is excellent in that, for example, the metal base and the surface lubricating layer can be fixed together by one coating operation without resorting to a plurality of operations such as a primer treatment.

Figure 2A:
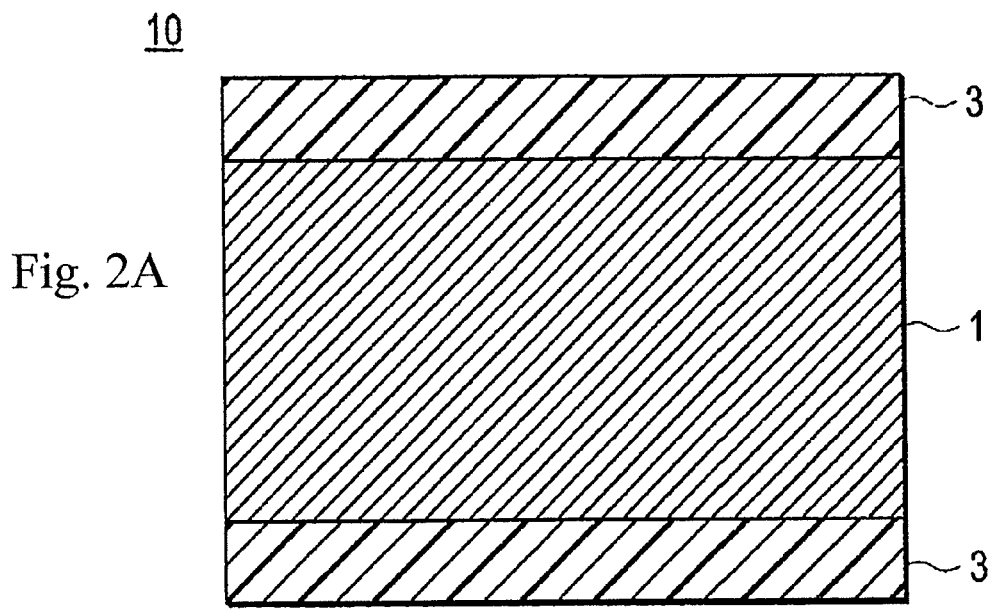
FIG. 2A is a partial sectional view schematically showing a laminate structure of a surface according to another embodiment, disclosed by way of example, of a medical device having surface lubricity in a wet state.
Figure 2B:
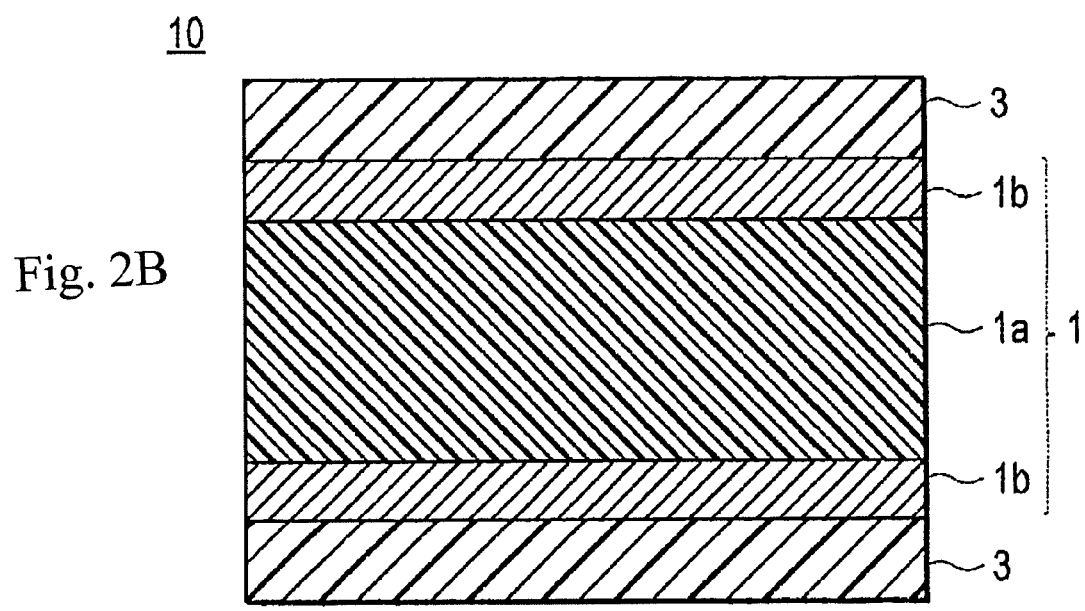
FIG. 2B is a partial sectional view schematically showing another laminate structure of a surface according to the another embodiment.

FIG. 2A is a partial sectional view schematically showing a laminate structure of a surface of another embodiment of the medical device disclosed by way of example and having surface lubricity in a wet state. FIG. 2B is a partial sectional view schematically showing another lamination structure.

As shown in FIGS. 2A and 2B, one example of a medical device 10 includes a base layer 1 made of a metal material and a surface lubricating layer 3 covering at least a part of the base layer 1 (in the figures, there is shown an instance where the base layer in the figures is entirely covered), wherein the surface lubricating layer 3 is obtained by forming a crosslinked structure by reaction between a compound having a plurality of thiol groups in the molecule and a hydrophilic polymer having a reactive functional group, and the surface lubricating layer 3 is bonded to the base layer 1 made of a metal material through the thiol group left in the crosslinked structure. For example, such a device can be employed wherein the surface lubricating layer 3 is obtained by coating, onto the base layer 1, a mixed solution dissolving, in a solvent, a compound having a plurality of thiol groups in the molecule and a hydrophilic polymer having a reactive functional group, followed by reaction between the thiol groups and the reactive functional group.

Each constituent member of the medical device of this disclosed embodiment is described in detail below.

(1) Base Layer 1

The base layer 1 of the medical device 10 is one that is made of a metal material.

The base layer 1 "made of a metal material" means that at least a surface of the base layer 1 can be constituted of a metal material, not always limited to one wherein the base layer 1 is constituted (formed) entirely (fully) of a metal material. Accordingly, the case where, as shown in FIG. 2B, the surface of a base layer core portion 1a formed of a resin material or the like is covered (coated) with a metal material by an appropriate method (for example, plating, metal deposition, sputtering or the like) to form a surface metal layer 1b is embraced within the scope of the base layer 1. Accordingly, the base layer core portion 1a can be in the form of a multi-layered structure wherein multiple layers of different types of materials are laminated, or a structure (composite body) wherein members formed of different types of materials for individual portions of a medical device are connected with one another. For example, a different type of middle layer (not shown) may be further formed between the base layer core portion 1a and the surface metal layer 1b. Additionally, as to the surface metal layer 1b, it may be in the form of a multi-layered structure wherein multiple layers of different types of metal materials are laminated, or a structure (composite body) wherein members formed of different types of metal materials for individual portions of a medical device are connected with one another.

No specific limitation is placed on the type of material usable for the base layer core portion 1a. A material capable of satisfactorily developing a function as an optimal base layer core portion 1a can be appropriately chosen depending on, for example, the application as a catheter, a guide wire, an injection needle or the like. For example, there can be exemplified organic (polymer) materials including polyolefins, modified polyolefins, polyethers, polyurethanes, polyamides, polyimides, polyesters and copolymers thereof, inorganic (polymer) materials such as various types of ceramic materials, and organic-inorganic composite materials although not limited thereto.

The metal materials usable as the base layer 1 or the surface metal layer 1b can be capable of bonding to the thiol group and can include various types of stainless steels (SUS) such as SUS304, gold, platinum, silver, copper, nickel, cobalt, titanium and alloys thereof such as nickel-titanium (Ni—Ti) alloy, nickel-cobalt (Ni—Co) alloy and the like. These may be used singly or in combination of 2 or more. A suitable metal material for an intended end use as a metal base of a catheter, a guide wire, an injection needle or the like can be appropriately chosen.

The base layer is not specifically limited in shape and can be selected from, for example, sheet, wire, tubular forms and the like depending on, for example, the manner of use.

For a material usable as the middle layer (not shown), no limitation is placed specifically thereon, and can be selected from, for example, materials capable of satisfactorily developing the function of bonding between the base layer core portion 1a and the surface metal layer 1b. For example, there may be exemplified organic (polymer) materials such as polyolefins, modified polyolefins, polyethers, polyurethanes, polyamides, polyimides, polyesters and copolymers thereof, inorganic (polymer) materials such as various types of ceramic materials, and organic-inorganic composite body although not limited thereto in any way.

(2) Surface Lubricating Layer 3

The surface lubricating layer 3 constituting the medical device of an exemplary embodiment is one that covers at least a part of the base layer 1 (in the figure, an instance is shown where the base layer in the figures is entirely covered) and contains a hydrophilic polymer having a reactive functional group and a compound having a plurality of thiol groups in the molecule.

The hydrophilic polymer can have a reactive domain where monomers having a reactive functional group gather together and a hydrophilic domain where hydrophilic monomers gather together.

The reason why the surface lubricating layer 3 is defined as covering at least a part of the base layer 1 is as follows: in medical devices for intended use such as catheters, guide wires, injection needles and the like, it is not necessarily required that all the surfaces (entire surface) of these medical devices have lubricity in wet state, but the surface lubricating layer 3 can be formed so as to cover only a surface portion (either a part or a whole) required to show surface lubricity in wet state.

(2a) Thickness of the Surface Lubricating Layer 3

The surface lubricating layer 3 of this disclosed example of the medical device can have a thickness, for example, only enough to permit the surface lubricating layer 3 to be strongly fixed to the base layer 1 made of metal material and permanently show excellent surface lubricity in use. The thickness of the surface lubricating layer 3 in non-swollen state can be 0.5 to 5 μm, for example, 1 to 5 μm. If the thickness of the surface lubricating layer 3 in non-swollen state is less than 0.5 μm, it can be difficult to form a uniform film, with the possibility that surface lubricity in wet state is not satisfactorily shown. On the other hand, when the thickness of the surface lubricating layer 3 in non-swollen state exceeds 5 μm, there is concern that when the medical device is inserted into the blood vessel or the like within a living body, swelling of such a thick surface lubricating layer may lead to the damage of the inner tissue of the blood vessel or the like, or is unlikely to permit passage of the medical device upon passage through a site (for example, an interior of peripheral vessel or the like) wherein a clearance between the blood vessel or the like and the medical device is small.

(2b) Method for Forming the Surface Lubricating Layer 3 (Bonding Forms of Between the Base Layer 1-the Surface Lubricating Layer 3)

According to one disclosed example, the surface lubricating layer 3 is obtained by forming a crosslinked structure by reaction between a compound having a plurality of thiol groups in the molecule ("thiol compound") and a hydrophilic polymer having a reactive functional group ("hydrophilic polymer") and the surface lubricating layer 3 is bonded to the base layer 1, made of a metal material, through the residual thiol group in the crosslinked structure.

Accordingly, where the surface lubricating layer 3 is formed, a mixed solution dissolving, in a solvent, the compound having a plurality of thiol groups in the molecule and the hydrophilic polymer having a reactive functional group (for example, an epoxy group) (hereinafter referred to simply as "mixed solution") can be coated onto the base layer, followed by reaction between the thiol compound and the reactive functional group to obtain the layer.

The techniques of coating (applying) the mixed solution onto the base layer 1 are not specifically limited, for which hitherto known methods may be applied including an immersion method (dipping method), a coating/printing method, a spray method, a spin coating method, a mixed solution impregnated sponge coating method and the like.

Techniques of reaction between the thiol compound and the reactive functional group are not specifically limited and hitherto known methods may be applied including, for example, heat treatment, light irradiation, electron beam irradiation, radiation irradiation, plasma irradiation and the like.

For example, an embodiment is now described in detail and by way of example, in which the base layer 1 is immersed in a mixed solution to coat the mixed solution (coating solution) onto the base layer 1, followed by heating operations to react the thiol compound and the reactive functional group of the hydrophilic polymer to form a crosslinked structure thereby preparing a surface lubricating layer 3 simultaneously with the thiol group left in the crosslinked structure being bonded to the metal material of the surface of the base layer 1. In this regard, the invention should not be construed as limited to these coating and reaction treatment operations. It will be noted that with this exemplary embodiment, if the system is reduced in pressure for defoaming in a state of the base layer 1 being immersed in the mixed solution, the solution can be quickly infiltrated into the fine, narrow inner surfaces of a medical device such as a catheter, a guide wire, an injection needle or the like thereby permitting the formation of the surface lubricating layer 3 to be facilitated.

Where the lubricating surface layer 3 is formed only on a part of the base layer 1, the mixed solution (coating solution) is coated only onto the part of the base layer 1 by immersing only the part of the base layer 1 in the mixed solution, after which heating operations are carried out to cause the reaction, whereupon the surface lubricating layer 3 in the form of a crosslinked structure of the hydrophilic polymer and the thiol compound can be formed on a desired surface portion of the base layer 1.

If it is difficult to immerse only a part of the base layer 1 in the mixed solution, the surface lubricating layer 3 can be formed on a desired surface portion of the base layer 1 by preliminarily protecting (covering) a surface portion of the polymer base layer 1, not to be formed with the surface lubricating layer 3, with an attachable or detachable appropriate member or material, subsequently immersing the base layer 1 in the mixed solution to coat the mixed solution on the base layer 1, followed by removing the protecting member (material) from the surface portion of the base layer 1 where the surface lubricating layer 3 is not to be formed and causing the reaction by heating operations. In this regard, however, the invention is not limited to these formation methods, but the surface lubricating layer 3 can be formed by appropriately utilizing conventionally known methods. For example, if immersing only a part of the base layer 1 in the mixed solution is difficult, other coating techniques (for example, a coating method, a spray method or the like) may be applied to in place of the immersion method. Nevertheless, in an exemplary embodiment where both an outer surface and an inner surface of a cylindrical device should have surface lubricity in wet state in view of the structure of the medical device (see the configurations of FIGS. 1A and 1B and FIGS. 2A and 2B), the immersion method (dipping method) is excellent in that both outer and inner surfaces can be coated at one time.

(2c) Each Compositions and Blending Ratio of the Mixed Solution (2c-1) Thiol Compound Used in the Mixed Solution As a thiol compound used in the mixed solution for forming the surface lubricating layer 3, no specific limitation is placed thereon so far as compounds having a plurality of thiol groups in the molecule are used, and such compounds may be any of linear, branched linear and cyclic compounds. Examples include compounds having 2 thiol groups in the molecule such as 1,2-ethanedithiol, 1,2-propanedithiol, 1,3-propanedithiol, 1,4-butanedithiol, 2,3-butanedithiol, 1,5-pentanedithiol, 1,6-hexanedithiol, 1,8-octanedithiol, 3,6-dioxa-1,8-octanedithiol, bis(2-mercaptoethyl)ether, bis(2-mercaptoethyl)sulfide, 1,2-benzenedithiol, 1,4-benzenedithiol, 1,4-bis(mercaptomethyl)benzene, toluene-3,4-dithiol, 1,5-dimercaptonaphthalene, 2,6-dimercaptopurine, 4,4'-biphenyldithiol, 4,4'-thiobisbenzenethiol, tetraethylene glycol bis(3-mercaptopropionate) and the like, compounds having 3 thiol groups in the molecule such as 1,3,5-benzenetrithiol, tris-[(3-mercaptopropionyloxy-ethyl)-isocyanurate, triazine trithiol, trimethylolpropane tris(3-mercaptopropionate) (TMMP) and the like, compounds having 4 thiol groups in the molecule such as pentaerythritol tetrakis(mercaptoacetate), pentaerythritol tetrakis(3-mercaptopropionate) and the like, compounds having 6 thiol groups in the molecule such as dipentaerythritol hexakis(3-mercaptopropionate) and the like, and derivatives and polymers thereof. These may be used singly or in combination of 2 or more.

The thiol compounds are not limited to the above-exemplified ones and other types of thiol compounds may also be usable, for example, if they are able to effectively develop the effect of the invention.

(2c-2) Hydrophilic Polymer Used in the Mixed Solution

The hydrophilic polymer serving as a constituent of the surface lubricating layer 3 and having a reactive functional group can be obtained, for example, by copolymerizing a monomer having a reactive functional group in the molecule and a hydrophilic monomer.

The hydrophilic polymer may be either a homopolymer composed of repeating units of 1 type or a copolymer composed of repeating units of 2 or more types, which may be a star-like, comb-like, random, graft, cyclic, block copolymer and the like. For example, mention is made of copolymers composed of 2 or more types of repeating units, for example, binary copolymers, for example, graft copolymers and block copolymers.

For example, the hydrophilic polymer can include block or graft copolymers from the standpoint that monomers having a reactive functional group (repeating units having a reactive functional group) gather together to form a reactive domain and hydrophilic monomers (repeated units having a hydrophilic site in a hydrophilic polymer) gather together to form a hydrophilic domain. With the block or graft copolymer, good results can be obtained in respect of the strength and lubricity of the surface lubricating layer.

No limitation is placed on the method of preparing (polymerization method) these hydrophilic polymers. The preparation is feasible by application of conventionally known polymerization methods such as, for example, a living radical polymerization method, a polymerization method using macromonomers, a polymerization method using a polymerization initiator such as a macro azo initiator or the like, a polycondensation method and the like.

(2c-2-a) Monomer Having a Reactive Functional Group

As such a monomer having the above reactive functional group, no limitation is placed thereon, for example, so long as it has reactivity with a thiol group. For example, mention is made of monomers having an epoxy group such as glycidyl acrylate, glycidyl methacrylate and the like, and monomers having an isocyanate group in the molecule, such as acryloyloxyethyl isocyanate. Of these, monomers having an epoxy group, such as glycidyl acrylate, glycidyl methacrylate and the like, can be employed in an exemplary embodiment. This is because they have, as a reactive functional group, an epoxy group that is excellent in reactivity with a thiol group, the reaction is promoted by application of heat, a crosslinked structure is formed and thus becomes insolubilized to easily form a surface lubricating layer, and handling is relatively easy. The hydrophilic polymer making use of monomers having an epoxy group is gentler in reaction rate (appropriate rate) in the course of the reaction such as by heating operations than hydrophilic polymers making use of monomers having an isocyanate group in the molecule. Accordingly, because the reaction rate is so gentle (appropriate rate) as to suppress or control the lowering of lubricity ascribed to the rise of a crosslinking density of the surface lubricating layer after gelation or solidification by immediate reaction in the course of the reaction such as under heating operations or in the course of the reaction with a thiol compound or mutual crosslinking reaction between reactive functional groups, handleability is considered as good. The monomers having these reactive functional group may be used singly or in combination of 2 or more.

(2c-2-b) Hydrophilic Monomer

As the hydrophilic monomer, any one may be used, for example, so long as it develops lubricity in a body fluid or an aqueous solvent and thus, no limitation is placed thereon. For example, mention can be made of acrylamide and derivatives thereof, vinyl pyrrolidone, acrylic acid or methacrylic acid and derivatives thereof, and monomers having a sugar or phospholipid at a side chain. Specific examples include N-methylacrylamide, N,N-dimethylacrylamide, acrylamide, acryloyl morpholine, N,N-dimethylaminoethyl acrylate, vinyl pyrrolidone, 2-methacryloyloxyethylphosphoryl choline, 2-methacryloyloxyethyl-D-glucoside, 2-methacryloyloxyethyl-D-mannoside, vinyl methyl ether, hydroxyethyl methacrylate and the like. From the standpoint of the ease in synthesis and operability, N,N-dimethylacrylamide can be employed. These monomers having the reactive functional group may be used singly or in combination of 2 or more.

(2c-3) Amount of a Thiol Compound in the Mixed Solution

In case where a thiol compound and a hydrophilic polymer are mixed and coated, the amount of the thiol compound added is not specifically limited. If the amount of a thiol compound is too large relative to the hydrophilic polymer, the surface lubricity lowers owing to an increase in crosslinked structure of the surface lubricating layer. Hence, the amount of the thiol compound added to the mixed solution (coating solution) should preferably remain, for example, within a range not greatly influencing the surface lubricity.

Figure 9:
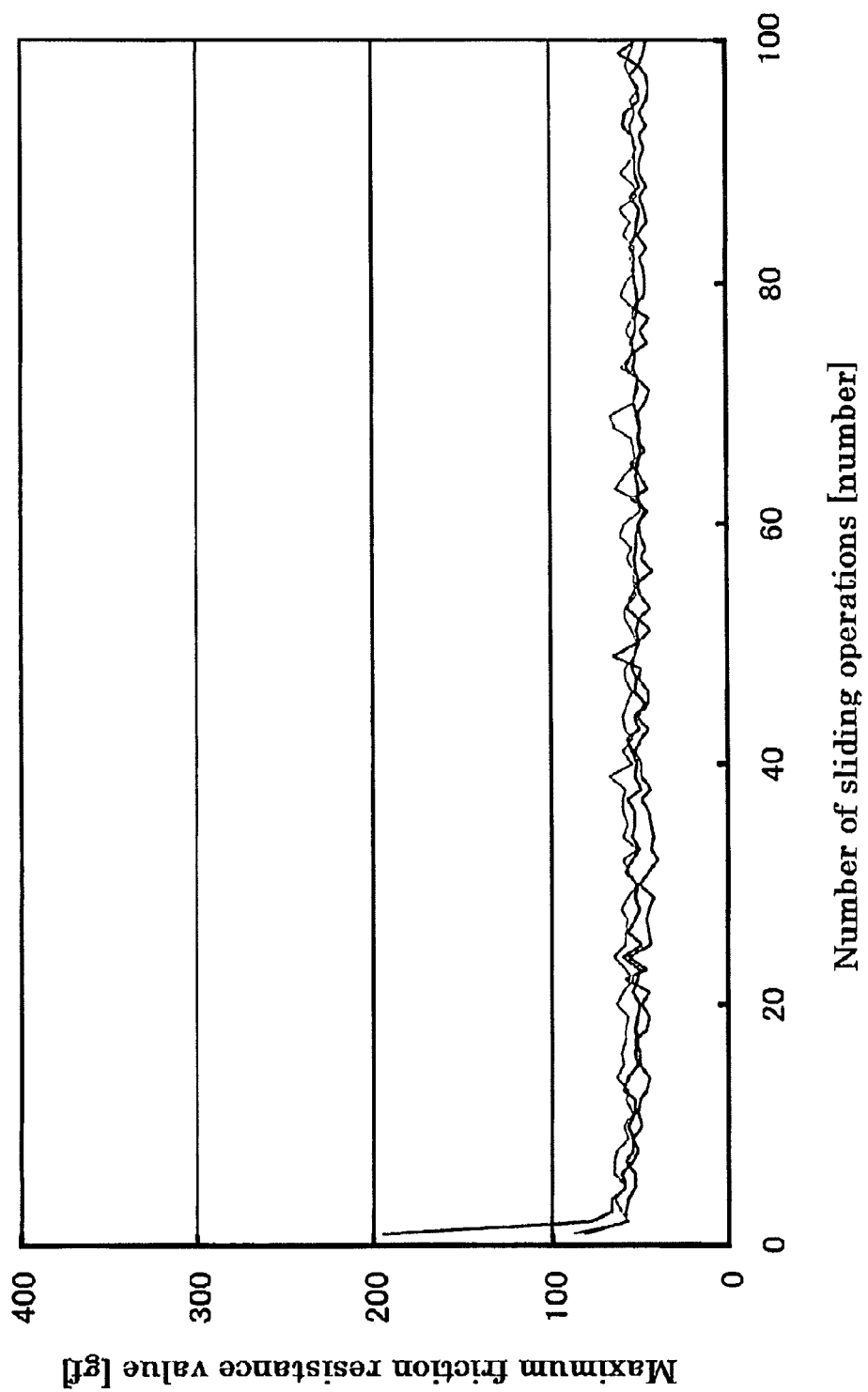
FIG. 9 is a graph showing the results of the evaluation test of the surface lubrication retention of a sheet (sample) of an example of a medical device having surface lubricity in a wet state obtained in Example 4.
Figure 10:
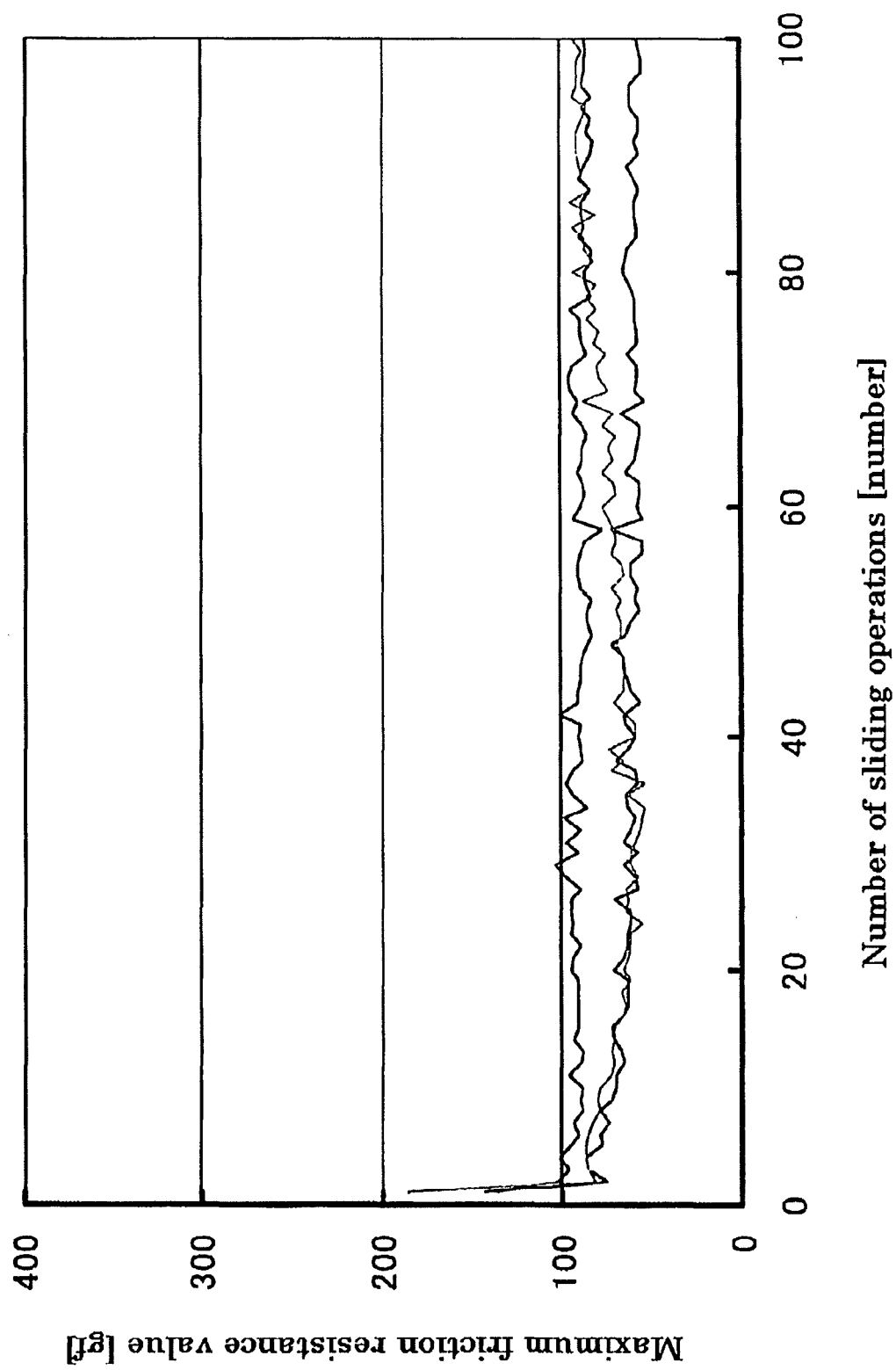
FIG. 10 is a graph showing the results of the evaluation test of the surface lubrication retention of a sheet (sample) of an example of a medical device having surface lubricity in a wet state obtained in Example 5.
Figure 11:
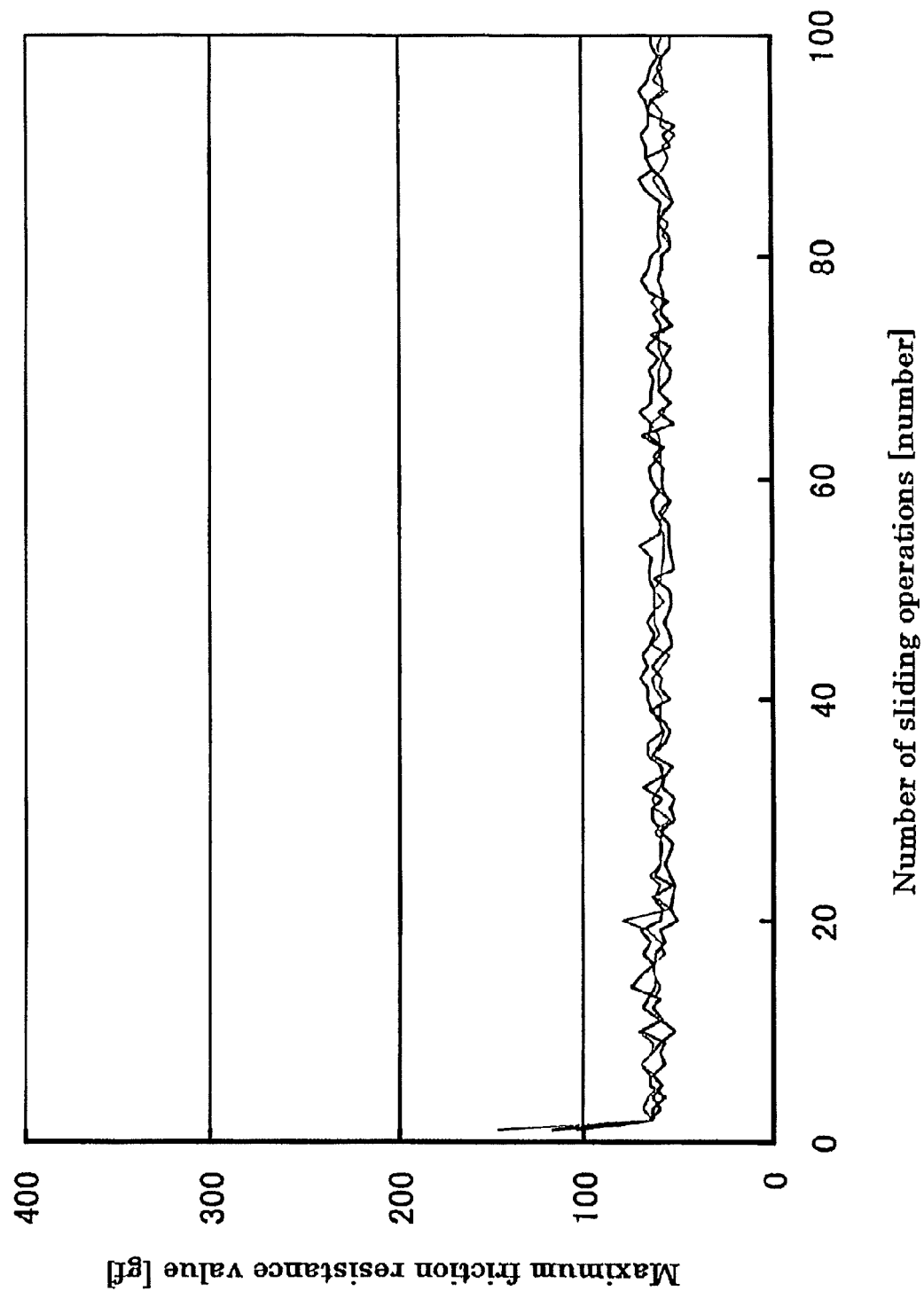
FIG. 11 is a graph showing the results of the evaluation test of the surface lubrication retention of a sheet (sample) of an example of a medical device having surface lubricity in a wet state obtained in Example 6.

An optimal amount of the thiol compound added to the mixed solution (coating solution) can differ depending on the number of thiol groups in the molecule of the thiol compound and the amount of the reactive functional group of the hydrophilic polymer to be reacted. For example, the amount can be 0.1 to 30 parts by weight, for example, 0.5 to 15 parts by weight relative to the hydrophilic polymer. If the amount of the thiol compound is less than 0.1 part by weight relative to the hydrophilic polymer, there is concern that insufficient bonding between the thiol group and the metal material on the surface of the base layer 1 results. On the other hand, the amount of the thiol compound exceeds 30 parts by weight relative to the hydrophilic polymer, there is concern that the surface lubricity in wet state lowers owing to an increase in crosslinking density of the surface lubricating layer. When the amount of the thiol compound is set at 0.5 to 15 parts by weight relative to the hydrophilic polymer, the amount of a thiol compound serving as a crosslinking agent for the surface lubricating layer can be optimized, thus being excellent in that the rise in crosslinking density of the surface lubricating layer can be suppressed, the surface lubrication retention (durability) can be enhanced, and excellent surface lubricity in use can be effectively kept over a long term (see, by comparison, FIGS. 9 to 11 showing the results of the evaluation tests of surface lubrication retention in Examples 4 to 6).

(2c-4) Concentration in the Mixed Solution

From the standpoint of obtaining a surface lubricating layer 3 of a desired thickness, for example, the concentration in the mixed solution (a total amount of a thiol compound and a hydrophilic polymer relative to a solvent) can be 0.1 to 2 wt %, for example, 0.5 to 15 wt %, for example, 1 to 10 wt %. If the concentration in the mixed solution is less than 0.1 wt %, there is a concern that the above-stated immersion operations have to be repeated plural times so as to obtain a surface lubricating layer 3 of a desired thickness and thus, a production efficiency lowers. On the other hand, where the concentration in the mixed solution exceeds 20 wt %, the viscosity of the mixed solution can become too high to coat a uniform film, simultaneously with a difficulty in quickly coating a fine, narrow inner surface of a medical device such as a catheter, a guide wire, an injection needle or the like. In this regard, however, a concentration outside the above range may be adequately usable if it is within a range not influencing the effect of the invention.

(2c-5) Solvent Used in the Mixed Solution

The solvent used in the mixed solution can include, for example, N,N-dimethylformamide (DMF), chloroform, acetone, tetrahydrofuran, dioxane, benzene or the like although not limited thereto in any way. These may be used singly or in combination of 2 or more.

(2d) Reaction Conditions (Heating Conditions) for Forming the Surface Lubricating Layer 3

For the formation of the surface lubricating layer 3, the reactive functional group (for example, an epoxy group) of a hydrophilic polymer and the thiol group of a thiol compound are reacted such as, for example, by heating operations or the like.

Such heating operations (reaction conditions) are not specifically limited, and can be capable of causing the reaction between the residual thiol group in a crosslinked structure (in the thiol compound) and the metal material on the surface of the base layer 1 to proceed (be promoted) simultaneously with the reaction between the reactive functional group and the thiol group (the formation of the crosslinked structure by the reaction). For example, the heat treatment can be carried out at not lower than 40° C., for example, 50 to 150° C., for 15 minutes to 15 hours, for example, 30 minutes to 10 hours. If the heating temperature is lower than 40° C., there is concern that the reaction between the reactive functional group of a hydrophilic polymer and the residual thiol group of the intermediate layer 2 becomes slow. If the heating time is less than 15 minutes, the reaction scarcely proceeds, with concern that an unreacted hydrophilic polymer increases in amount simultaneously with some possibility that a difficulty is involved in securing a portion bonded with the surface of the base layer and keeping the surface lubricity over a long time. On the other hand, if the heating time exceeds 15 hours, a further effect ascribed to such heating is not obtained, thus being poor in economy.

No limitation is placed on the pressure conditions when in heat treatment. The treatment may be carried out not only under a normal pressure (atmospheric pressure), but also under increased pressure or under reduced pressure. Where the reactive functional group of a hydrophilic polymer is an epoxy group, a reaction catalyst such as a trialkylamine compound or a tertiary amine compound such as pyridine or the like may be added to the mixed solution timely in an appropriate amount so as to promote the reaction with the thiol group. For a heating means (apparatus), there can be utilized, for example, an oven, a dryer, a microwave heating apparatus and the like.

After the formation of the surface lubricating layer 3 by the heating operations, an excess hydrophilic polymer and thiol compound may be cleaned with an appropriate solvent thereby permitting the crosslinked structure alone (by the reaction between the reactive functional group and the thiol group), in which the surface lubricating layer 3 is strongly, directly fixed to the base layer 1, to be left thereat.

The thus formed crosslinked structure serving as the surface lubricating layer 3 can develop lubricity after absorption of water at a body temperature of a patient (30 to 40° C.).

The medical device having surface lubricity in a wet state as disclosed here can be used in contact with a body fluid or blood, and can have surface lubricity in a body fluid or an aqueous liquid such as a physiologically saline solution, and is capable of improving workability and reducing damage of tissue and mucous membranes. For example, mention is made of guide wires, catheters and the like used in the blood vessel. The following exemplary medical devices can be indicated.

(1) Catheters to be perorally or pernasally inserted or indwelled in digestive organs such as gastric catheters, nutrition catheters, tubes for tubal feeding and the like.

(2) Catheters to be perorally or pernasally inserted or indwelled in the respiratory tract or windpipe such as oxygen catheters, oxygen canulas, tubes or cuffs for endotracheal tube, tubes or cuffs for tracheostomy tube, endotracheal suctioning catheters and the like.

(3) Catheters to be inserted or indwelled in the urethral tube or urinary duct such as urethral catheters, urinary catheters, catheters or balloons for urethral balloon catheters and the like.

(4) Catheters to be inserted or indwelled in various body cavities, organs and tissues, such as suction catheters, drain catheters, rectal catheters and the like.

(5) Catheters to be inserted or indwelled in blood vessel, such as indwelling needles, IVH catheters, thermodilution catheters, angiographic catheters, vasodilatation catheters and dilators or introducers and the like, or guide wires, stylets and the like for these catheters.

(6) Artificial windpipes, artificial bronchial tubes and the like.

(7) Medical devices for extracorporeal circulation therapy (artificial lung, artificial heart, artificial kidney and the like) and circuits thereof.

EXAMPLES

Example 1

After ultrasonic cleaning of a SUS 304 sheet (30 mm long×50 mm wide×0.5 mm thick, a base layer made of a metal material) in acetone, the sheet was immersed in a DMF solution of tris-[(3-mercaptopropionyloxy)-ethyl]-isocyanurate (TEMPIC) (made by SC Organic Chemical Co., Ltd.) (3 thiol groups in one molecule) whose concentration was adjusted to 20 mM, and was heated in an oven of 130° C. for 3 hours to fix TEMPIC to the surface of the SUS 304 sheet. Thereafter, excess TEMPIC, not fixed to the surface of the metal (SUS 304 sheet), was removed by ultrasonic cleaning in DMF. In this way, an intermediate layer made of TEMPIC and covering the surface of the base layer (SUS 304 sheet) was formed (fixed).

The TEMPIC-fixed SUS 304 sheet was immersed in a DMF solution dissolving a block copolymer having polydimethylacrylamide (DMAA) as a hydrophilic domain and polyglycidyl methacrylate (GMA) as a reactive domain (DMAA:GMA (molar ratio)=11.5:1) at a concentration of 8 wt %, followed by reaction in an oven of 120° C. for 7 hours to form a surface lubricating layer having a thickness (in non-swollen state) of 3 μm so as to cover the surface of the intermediate layer made of TEMPIC, which was fixed to the surface of the base layer (SUS 304 sheet).

Figure 3A:
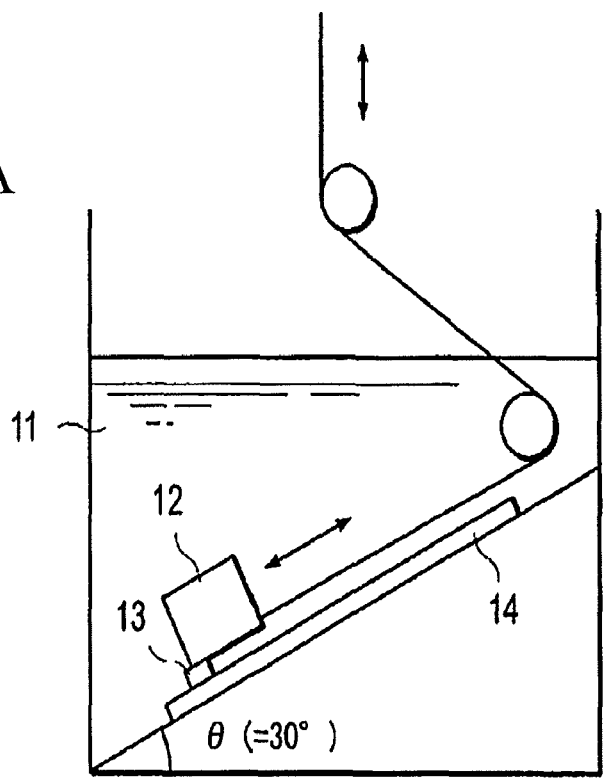
FIG. 3A is a schematic view of a testing apparatus for evaluating surface lubrication retention used in Examples.
Figure 3B:
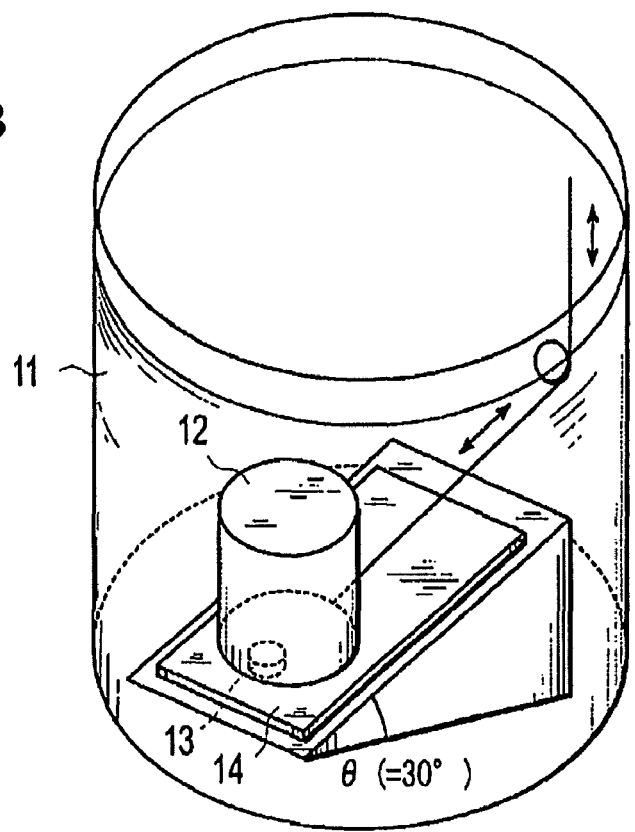
FIG. 3B is a perspective view of the testing apparatus used to evaluate the surface lubrication retention of FIG. 3A.

The sheet (sample) 14, on which the surface lubricating layer had been formed according to the above procedure, was fixed on a plate, in water 11, inclined to make an angle of 30° as shown in FIG. 3. A cylindrical brass weight 12 of 1 kg, to which a cylindrical polyethylene sheet 13 (φ 20 mm, R 1 mm) was attached, was gently placed on the surface lubricating layer 3 of the sheet (sample) 14. In this condition, the weight 12 was reciprocated 100 times up and down at a rate of 100 cm/min at width of 2 cm. The maximum friction resistance value in the respective reciprocating cycles was measured by autograph (AG-IS10 kN, made by SHIMADZU CORPORATION) to check the surface lubrication retention relative to 100 cycles of repeated sliding.

Figure 4:
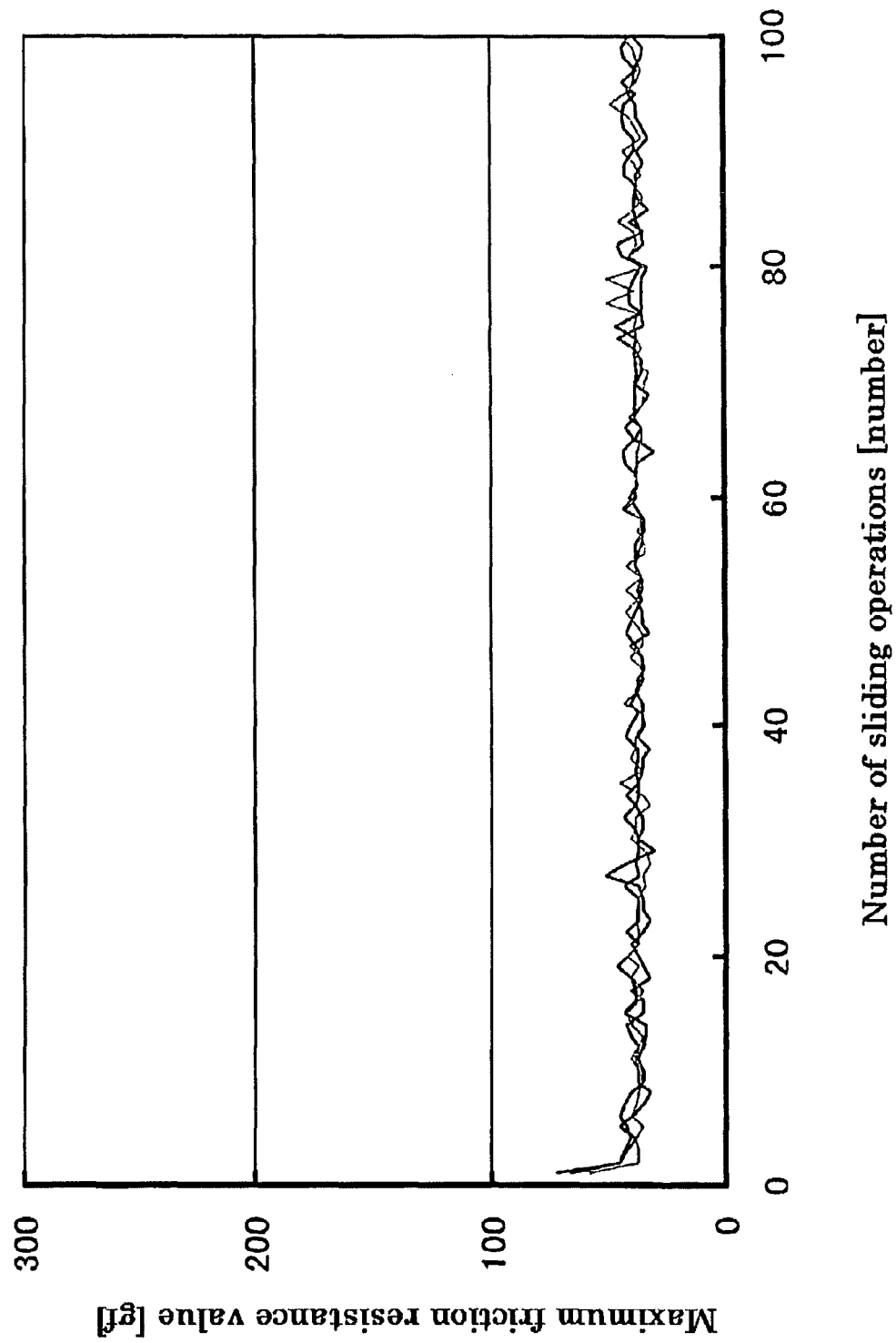
FIG. 4 is a graph showing the results of the evaluation test of the surface lubrication retention of a sheet (sample) of an example of a medical device having surface lubricity in a wet state obtained in Example 1.

As a result of the test, the maximum friction resistance values showed constant values as shown in FIG. 4 and thus, stable lubricity was shown in the 100 cycles of repeated sliding. In addition, the surface lubricating layer showed stable lubricity relative to the 500 cycles of repeated sliding. It will be noted that in FIG. 4, three samples were similarly tested and the respective results are shown in the figure. In the following FIGS. 5 to 12, three samples were also tested in a similar way and the respective results are shown.

Comparative Example 1

Figure 5:
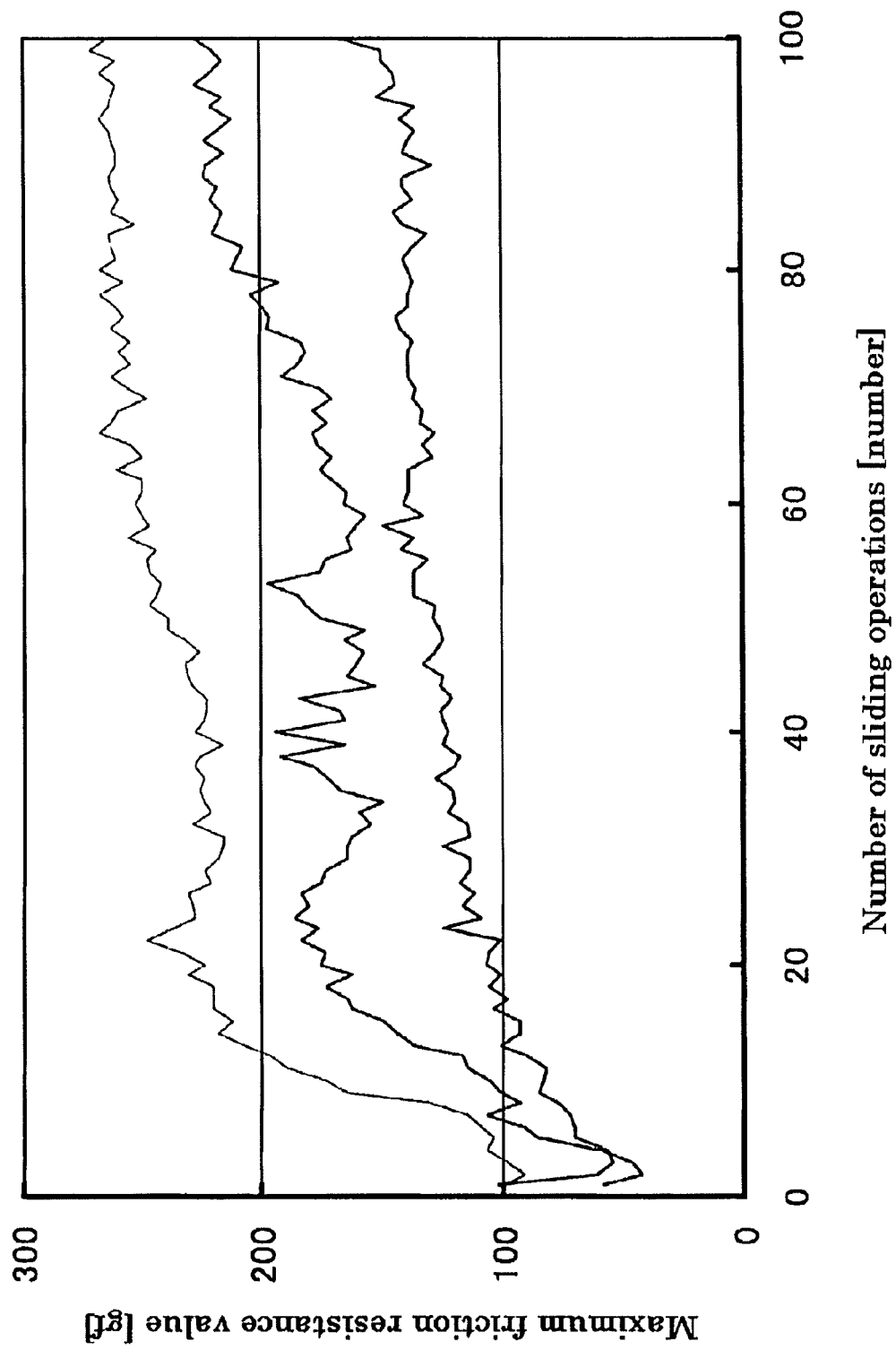
FIG. 5 is a graph showing the results of the evaluation test of the surface lubrication retention of a sheet (sample) of a medical device having surface lubricity in a wet state obtained in Comparative Example 1.

A surface lubricating layer having a thickness (in non-swollen state) of 3 μm was formed under the same treating conditions as in Example 1 except that the fixing treatment of TENPIC (formation of the intermediate layer) was omitted. Thereafter, the surface lubrication retention of the sheets (samples) was checked in the same manner as in Example 1, revealing that although the friction resistance values were initially low as shown in FIG. 5, the friction resistance values increased during repetitions of sliding, thus being poor in persistence of the surface lubricating layer.

Example 2

Figure 6:
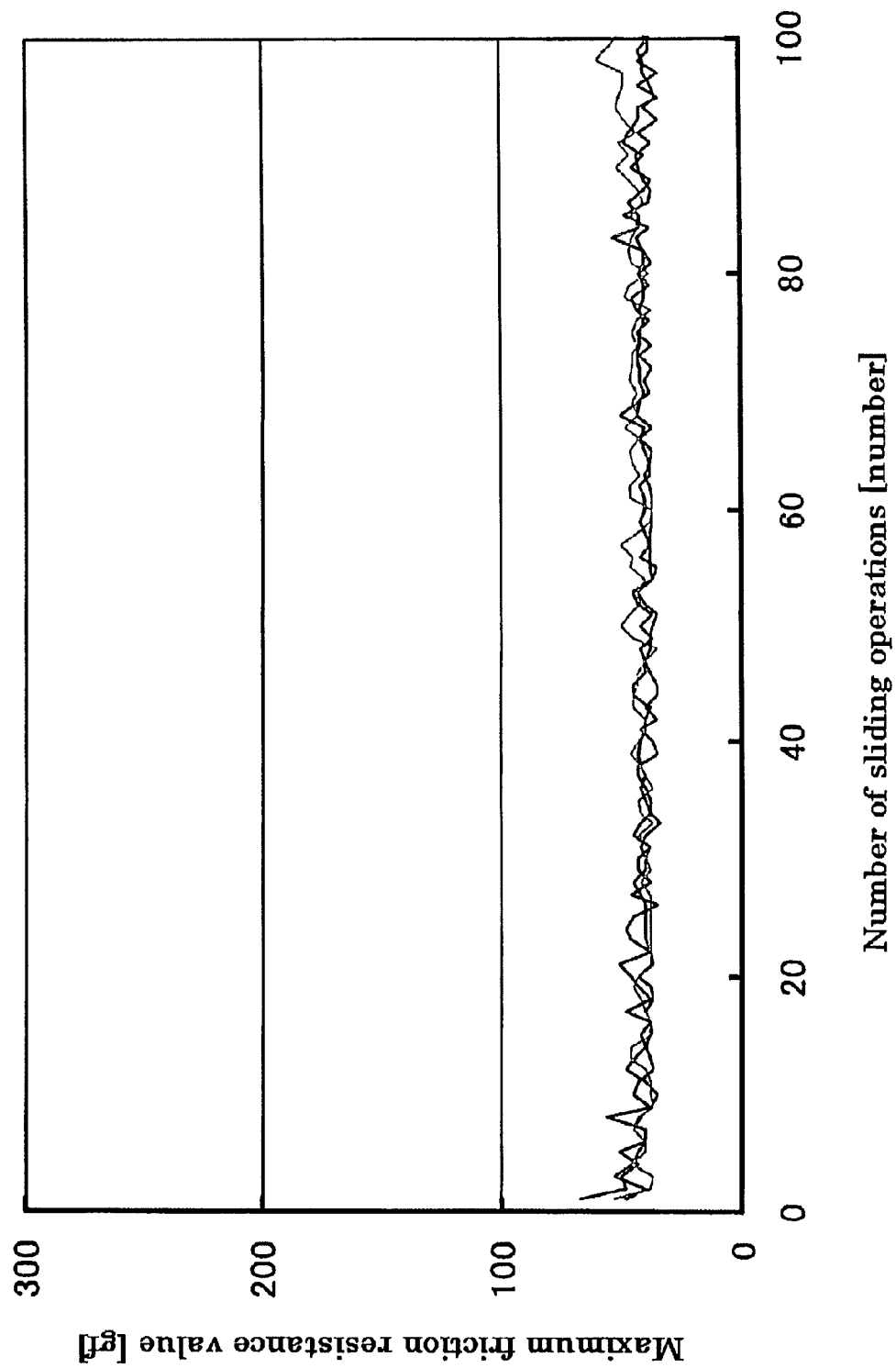
FIG. 6 is a graph showing the results of the evaluation test of the surface lubrication retention of a sheet (sample) of an example of a medical device having surface lubricity in a wet state obtained in Example 2.

In the same manner as in Example 1 except that TEMPIC of Example 1 was changed to dipentaerythritol hexakis(3-mercaptopropionate) (made by SC Organic Chemical Co., Ltd.) (6 thiol groups in one molecule), an intermediate layer and a surface lubricating layer having a thickness (in non-swollen state) of 3 μm were successively formed and surface lubrication retention was checked, revealing that the maximum friction resistance values were constant as shown in FIG. 6 and that stable lubricity was shown in 100 cycles of repeated sliding.

Example 3

Figure 7:
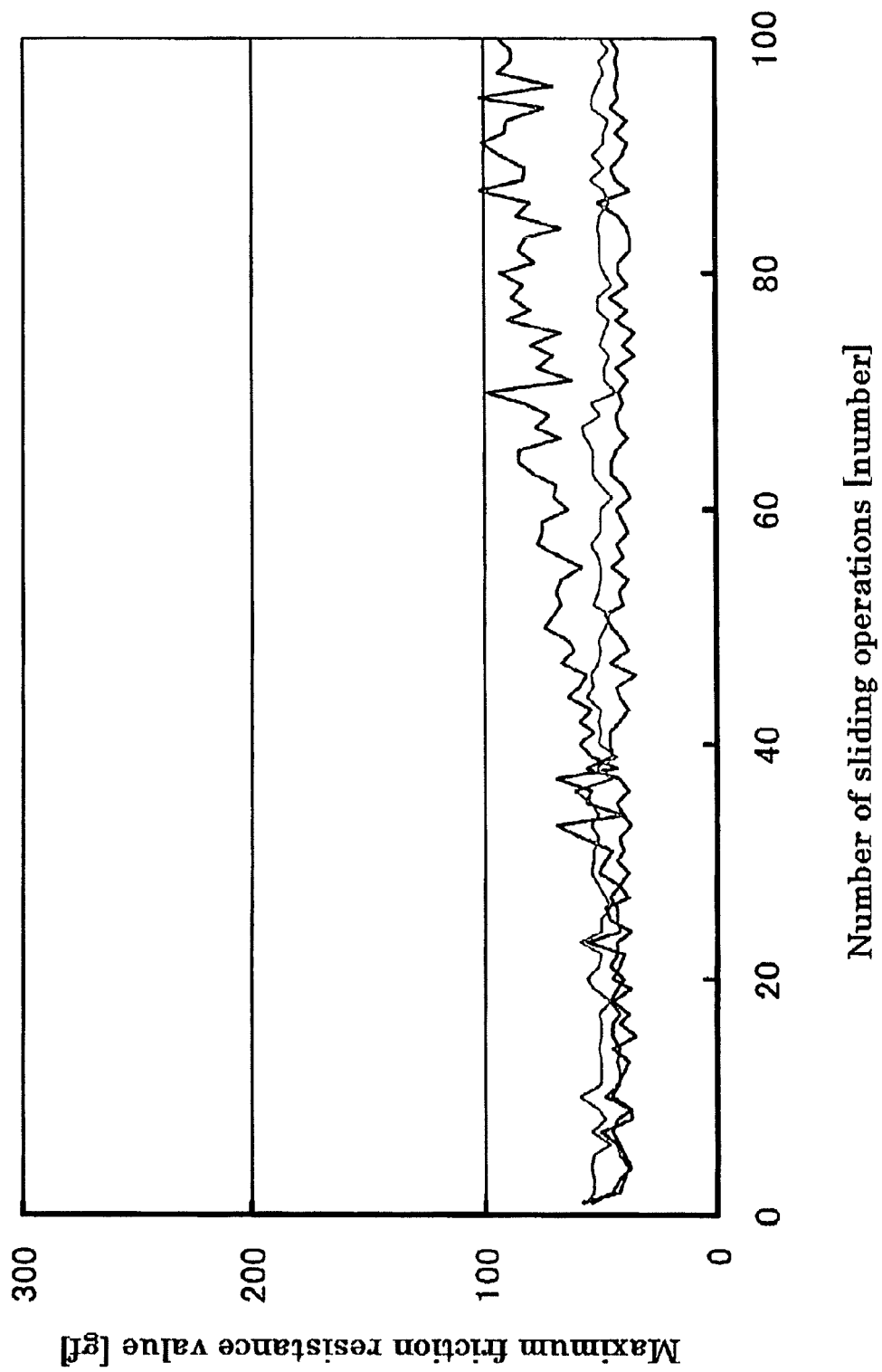
FIG. 7 is a graph showing the results of the evaluation test of the surface lubrication retention of a sheet (sample) of an example of a medical device having surface lubricity in a wet state obtained in Example 3.

In the same manner as in Example 1 except that TEMPIC of Example 1 was changed to tetraethylene glycol bis(3-mercaptopropionate)(made by SC Organic Chemical Co., Ltd.) (2 thiol groups in one molecule), an intermediate layer and a surface lubricating layer having a thickness (in non-swollen state) of 3 μm were successively formed, and surface lubrication retention was checked, revealing that two samples among the three samples showed constant maximum friction resistance values as shown in FIG. 7 and also showed stable lubricity in 100 cycles of repeated sliding. The other one sample was such that the maximum friction resistance values was observed to increase in the middle of repetitions, but small in the increment.

Comparative Example 2

Figure 8:
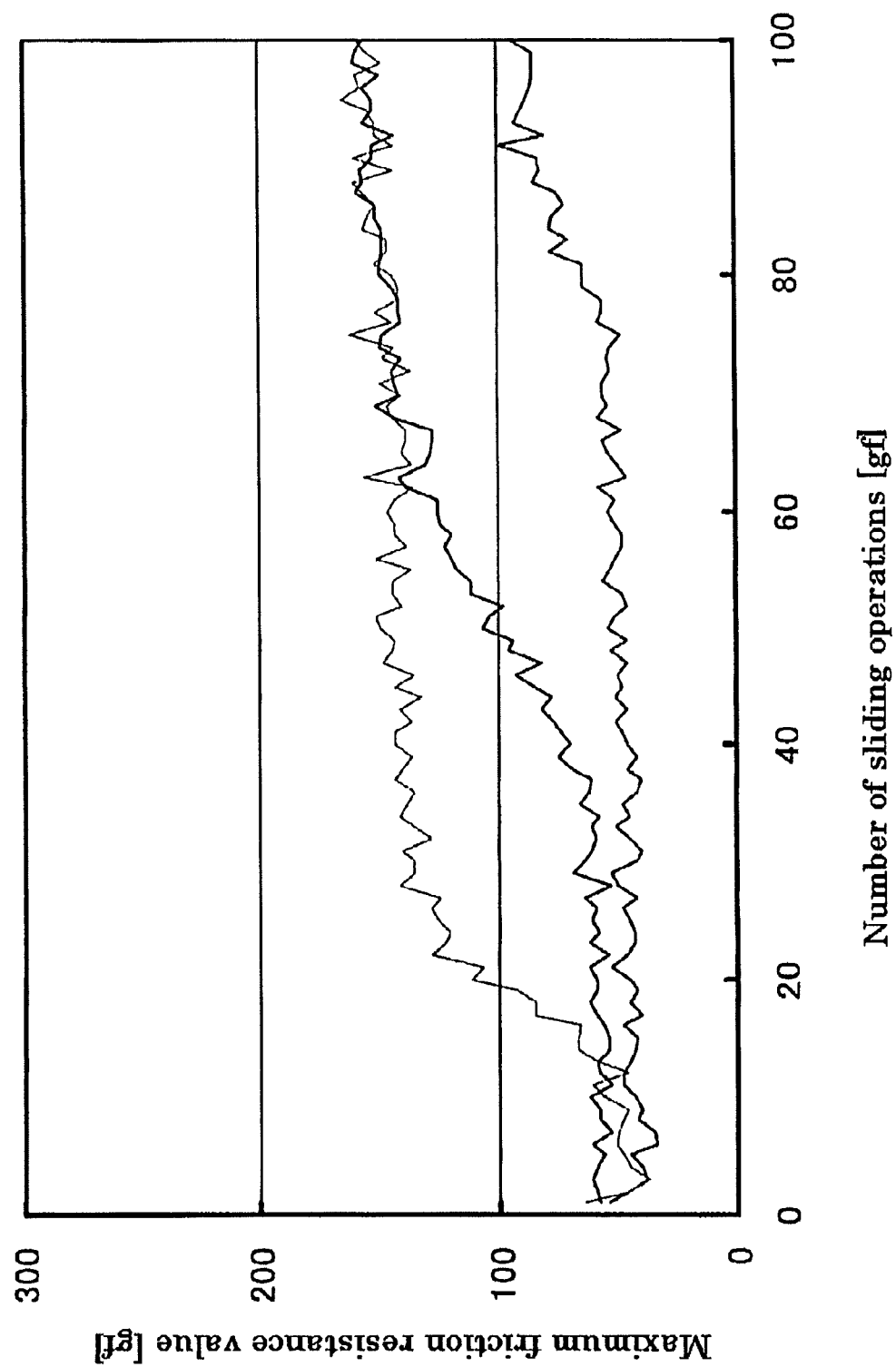
FIG. 8 is a graph showing the results of the evaluation test of the surface lubrication retention of a sheet (sample) of a medical device having surface lubricity in a wet state obtained in Comparative Example 2.

In the same manner as in Example 1 except that TEMPIC of Example 1 was changed to L-cysteine hydrochloride (Wako Pure Chemical Industries, Ltd.) (1 thiol group, 1 amino group and 1 carboxyl group in one molecule), an intermediate layer and a surface lubricating layer having a thickness (in non-swollen state) of 3 μm were successively formed, and surface lubrication retention was checked, revealing that the maximum friction resistance values changed as shown in FIG. 8 and although the persistence of the surface lubricating layer was improved over that of the non-treated sample (Comparative Example 1), the effect was lower compared with Examples 1 to 1

Example 4

TEMPIC was added to a DMF solution, in which the block copolymer (DMAA:GMA (molar ratio)=11.5:1) was dissolved at a rate of 8 wt %, in an amount of 12 parts by weight relative to the block copolymer to prepare a mixed solution, and a SUS 304 sheet (30 mm long×50 mm wide×0.5 mm thick, a base layer made of a metal material), which was subjected to ultrasonic cleaning in acetone, was immersed therein, followed by reaction in an oven of 120° C. for 7 hours to form a surface lubricating layer having a thickness (in non-swollen state) of 3 μm on the SUS 304 sheet. Subsequently, surface lubrication retention was checked in a similar way, revealing that the maximum friction values were constant as shown in FIG. 9 and stable lubricity was shown in 100 cycles of repeated sliding. The surface lubricating layer showed stable lubricity at 500 cycles of repeated sliding.

Example 5

Under the same treating conditions as in Example 4 except that the amount of TEMPIC added was changed to 20 parts by weight relative to the block copolymer, a surface lubricating layer having a thickness (in non-swollen state) of 3 μm was formed on the SUS 304 sheet. Thereafter, the surface lubrication retention of the sheet (sample) was checked in the same manner as in Example 1, revealing that although the maximum friction resistance values were higher than those of Example 4 as shown in FIG. 10, constant values were shown in the course of 100 cycles of repeated sliding and thus, stable lubricity was kept.

Example 6

Under the same treating conditions as in Example 4 except that the thiol compound added was changed from TEMPIC to tetraethylene glycol bis(3-mercaptopropionate) (made by SC Organic Chemical Co., Ltd.) (2 thiol groups in one molecule), a surface lubricating layer having a thickness (in non-swollen state) of 3 μm was formed on the SUS 304 sheet. Thereafter, surface lubrication retention was likewise checked, revealing that the maximum friction resistance values were constant as shown in FIG. 11 and stable lubricity was shown in 100 cycles of repeated sliding.

Comparative Example 3

Figure 12:
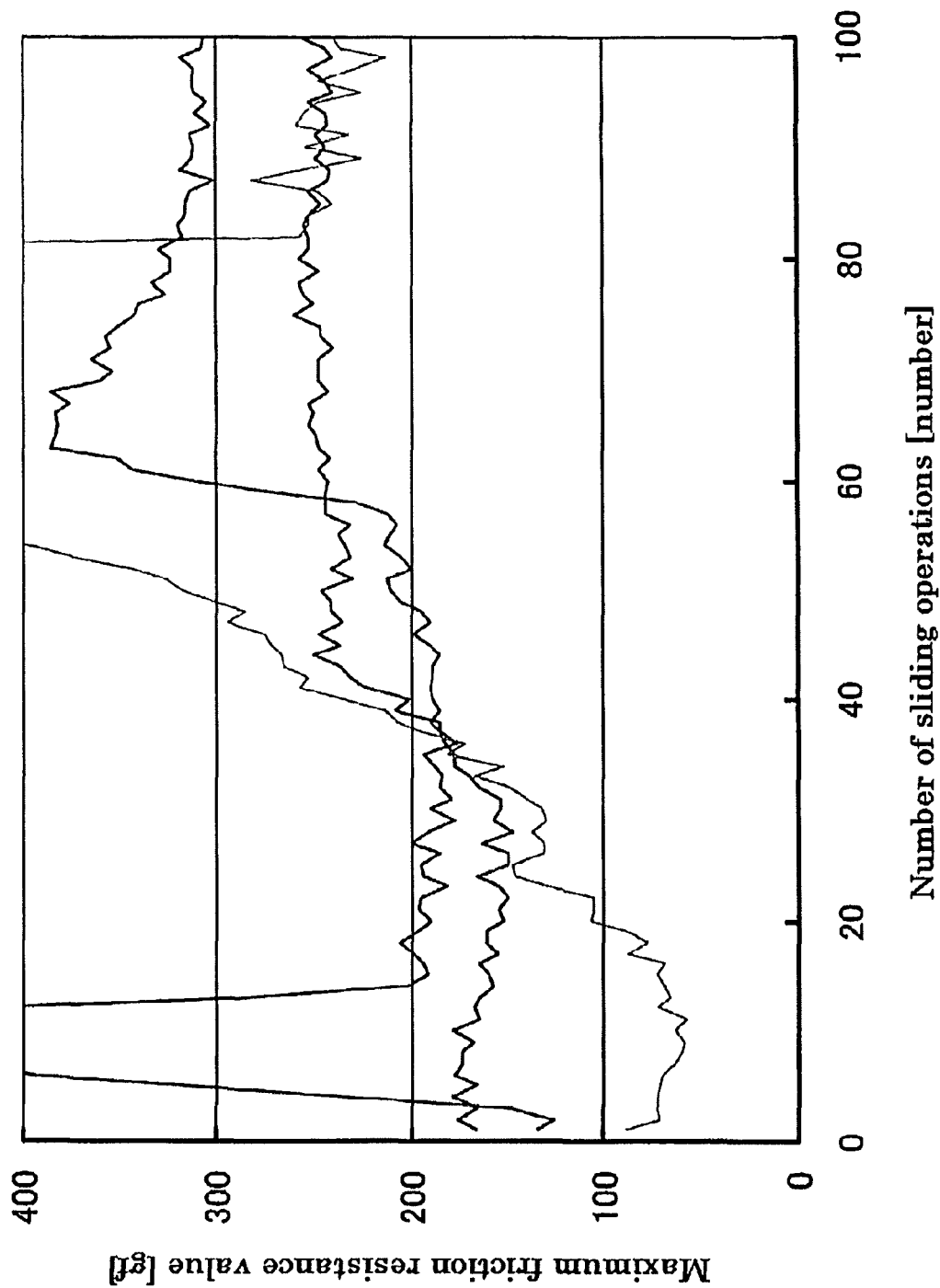
FIG. 12 is a graph showing the results of the evaluation test of the surface lubrication retention of a sheet (sample) of a medical device having surface lubricity in a wet state obtained in Comparative Example 3.

Under the same treating conditions as in Example 4 except that the thiol compound added was changed from TEMPIC to L-cysteine hydrochloride (made by Wako Pure Chemical Industries, Ltd.) (1 thiol group, 1 amino group and 1 carboxyl group in one molecule), a surface lubricating layer having a thickness (in non-swollen state) of 3 μm was formed on the SUS 304 sheet. Thereafter, surface lubrication retention was likewise checked, revealing that the maximum friction resistance values varied as shown in FIG. 12 and both surface lubricity and persistence were poor.

Example 7

A Ni—Ti wire (ϕ 0.5 mm, length 150 mm, a base layer made of a metal material) was subjected to ultrasonic cleaning in acetone and subsequently immersed in a DMF solution of TEMPIC whose concentration was adjusted to 20 mM, followed by heating in an oven of 130° C. for 3 hours to fix TEMPIC to the surface of the Ni—Ti wire. Thereafter, excess TEMPIC, not fixed to the surface of the metal (Ni—Ti wire), was removed by ultrasonic cleaning in DMF. In this way, the intermediate layer made of TEMPIC and covering the surface of the base layer (Ni—Ti wire) was formed (fixed).

After immersing the TEMPIC-fixed Ni—Ti wire in a DMF solution dissolving, at a rate of 8 wt %, a block copolymer (DMAA:GMA (molar ratio)=11.5:1) obtained from poly-dimethylacrylamide (DMAA) forming a hydrophilic domain and polyglycidyl methacrylate (GMA) forming a reactive domain, reaction was carried out in an oven of 120° C. for 7 hours to form a surface lubricating layer having a thickness (in non-swollen state) of 3 μm so as to cover the intermediate layer made of TEMPIC and fixed to the surface of the base layer (Ni—Ti wire).

The wire (sample) wherein the surface lubricating layer had been formed according to the above procedure was fixed inside a petridish filled with water, which was, in turn, fixed on a trolley table of a friction measuring apparatus (Tribomaster TL201Ts, made by Trinity Lab Co., Ltd.). A cylindrical terminal (SEBS, ϕ 10 mm) was brought into contact on the surface lubricating layer and a load of 300 g was imposed on the terminal. The trolley table set at a moving rate of 100 cm/min and a moving distance of 2.5 cm was horizontally reciprocated 100 times to measure friction resistance values. An average value of the maximum friction resistance values in every reciprocation was read out to evaluate surface lubrication retention relative to the 100 cycles of repeated sliding.

Figure 13:
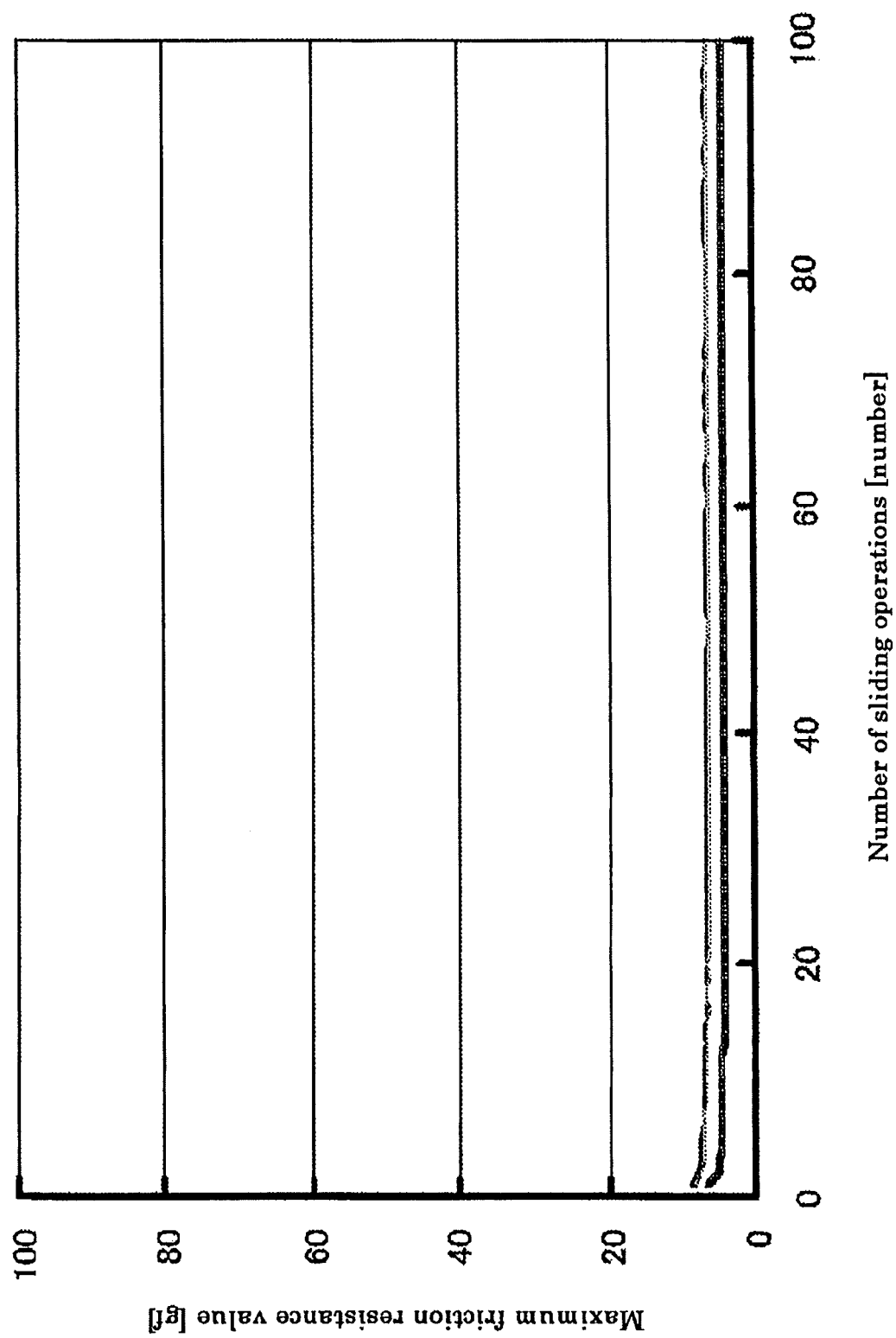
FIG. 13 is a graph showing the results of the evaluation test of the surface lubrication retention of a sheet (sample) of an example of a medical device having surface lubricity in a wet state obtained in Example 7.

As a result of the test, constant friction resistance values are shown as in FIG. 13, demonstrating stable lubricity in 100 cycles of repeated sliding. Also, this surface lubricating layer showed stable lubricity in 500 cycles of repeated sliding.

Comparative Example 4

Figure 14:
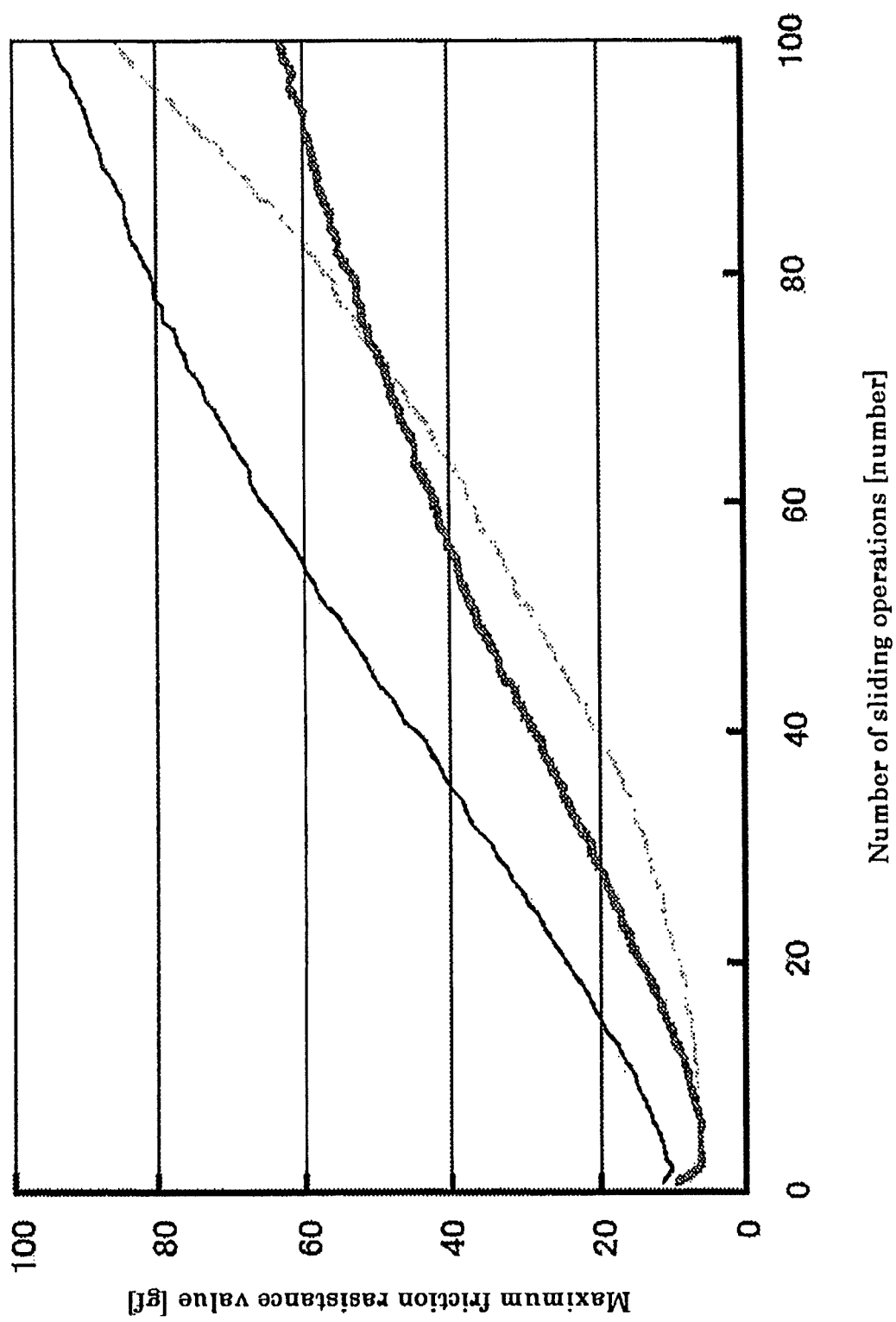
FIG. 14 is a graph showing the results of the evaluation test of the surface lubrication retention of a sheet (sample) of a medical device having surface lubricity in a wet state obtained in Comparative Example 4.

Under the same treating conditions as in Example 7 except that the fixing treatment with TEMPIC (formation of the intermediate layer) was omitted, a surface lubricating layer having a thickness (in non-swollen state) of 3 μm was formed. Thereafter, the surface lubrication retention of the wire (sample) was checked in the same manner as in Example 7, revealing that although low friction resistance values were initially shown as in FIG. 14, the friction resistance values increased during the repetitions of sliding, thus being poor in persistence of the surface lubricating layer.

Example 8

Figure 15:
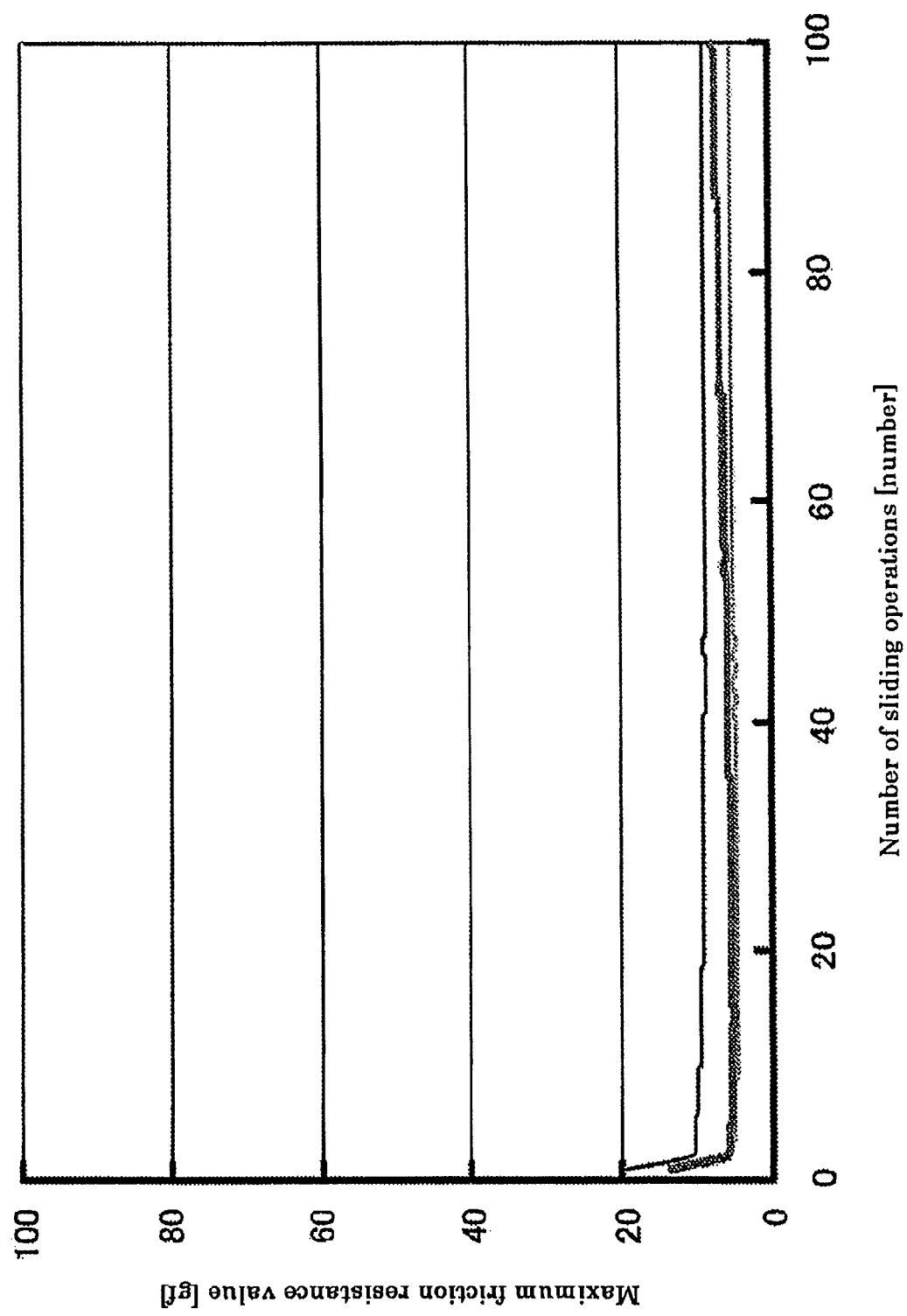
FIG. 15 is a graph showing the results of the evaluation test of the surface lubrication retention of a sheet (sample) of an example of a medical device having surface lubricity in a wet state obtained in Example 8.

TEMPIC was added to a DMF solution, in which the block copolymer (DMAA:GMA (molar ratio)=11.5:1) was dissolved at a rate of 8 wt %, in an amount of 2.5 parts by weight relative to the block copolymer to prepare a mixed solution, after which a Ni—Ti wire (ϕ 0.5 mm, length 150 mm, a base layer made of a metal material), which was subjected to ultrasonic cleaning in acetone, was immersed therein, followed by reaction in an oven of 120° C. for 7 hours to form a surface lubricating layer having a thickness (in non-swollen state) of 3 μm on the Ni—Ti wire. Subsequently, surface lubrication retention was checked in a similar way, revealing that the maximum friction values were constant as shown in FIG. 15 and stable lubricity was shown in 100 cycles of repeated sliding. The surface lubricating layer showed stable lubricity in the course of 500 cycles of repeated sliding.

The detailed description above describes features and aspects of embodiments, disclosed by way of example, of a medical device exhibiting surface lubricity in a wet state. The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A medical device having surface lubricity in a wet state, comprising:
    a base layer made of a metal material;
    an intermediate layer that covers at least a part of said base layer and is made of only a compound having three or more thiol groups in one molecule; and
    a surface lubricating layer that covers a surface of said intermediate layer and is made of a hydrophilic polymer having a reactive functional group,
    wherein said surface lubricating layer is bonded to said base layer through said intermediate layer by reaction between said compound having three or more thiol groups and said hydrophilic polymer,
    wherein the compound having three or more thiol groups in one molecule comprises tris-[(3-mercaptopropionyloxy)-ethyl]-isocyanurate, dipentaerythritol hexakis(3-mercaptopropionate) or a combination thereof.

2. The medical device having surface lubricity in a wet state according to claim 1, wherein the surface lubricating layer has a thickness in non-swollen state of 0.5 to 5 µm.

3. The medical device having surface lubricity in a wet state according to claim 1, wherein the hydrophilic polymer having a reactive functional group comprises an epoxy group or an isocyanate group.

4. A medical device having surface lubricity in a wet state, comprising:
    a base layer made of a metal material;
    an intermediate layer that covers at least a part of said base layer and is made of only a compound having three or more thiol groups in one molecule; and
    a surface lubricating layer that covers a surface of said intermediate layer and is made of a hydrophilic polymer having a reactive functional group,
    wherein said surface lubricating layer is bonded to said base layer through said intermediate layer by reaction between said compound having three or more thiol groups and said hydrophilic polymer.

5. The medical device having surface lubricity in a wet state according to claim 4, wherein the compound having three or more thiol groups in one molecule comprises tris-[(3-mercaptopropionyloxy)-ethyl]isocyanurate, dipentaerythritol hexakis(3-mercaptopropionate) or a combination thereof.

6. The medical device having surface lubricity in a wet state according to claim 4, wherein the surface lubricating layer has a thickness in non-swollen state of 0.5 to 5 µm.

7. The medical device having surface lubricity in a wet state according to claim 4, wherein the hydrophilic polymer having a reactive functional group comprises an epoxy group or an isocyanate group.

* * * * *